(12) United States Patent
Cramail et al.

(10) Patent No.: US 9,556,403 B2
(45) Date of Patent: Jan. 31, 2017

(54) METHOD FOR PREPARING POLYOLS AND PRODUCTS OBTAINED

(75) Inventors: Henri Cramail, Pessac (FR); Aurélie Boyer, Bourdeaux (FR); Eric Cloutet, Sant Caprais de Bordeaux (FR); Rachida Bakhiyi, Merignac (FR); Carine Alfos, Pessac (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 13/395,027

(22) PCT Filed: Sep. 10, 2010

(86) PCT No.: PCT/FR2010/051894
§ 371 (c)(1),
(2), (4) Date: Sep. 19, 2012

(87) PCT Pub. No.: WO2011/030076
PCT Pub. Date: Mar. 17, 2011

(65) Prior Publication Data
US 2013/0005937 A1    Jan. 3, 2013

(30) Foreign Application Priority Data
Sep. 11, 2009    (FR) ..................... 09 56260

(51) Int. Cl.
| | | |
|---|---|---|
| *C07C 67/31* | (2006.01) | |
| *C07D 405/12* | (2006.01) | |
| *C08G 18/36* | (2006.01) | |
| *C07C 69/675* | (2006.01) | |
| *C11C 3/00* | (2006.01) | |
| *C07C 67/03* | (2006.01) | |
| *C07C 69/732* | (2006.01) | |
| *C07D 303/40* | (2006.01) | |
| *C07D 303/42* | (2006.01) | |
| *C07D 303/44* | (2006.01) | |

(52) U.S. Cl.
CPC .............. *C11C 3/003* (2013.01); *C07C 67/03* (2013.01); *C07C 67/31* (2013.01); *C07C 69/732* (2013.01); *C07D 303/40* (2013.01); *C07D 303/42* (2013.01); *C07D 303/44* (2013.01); *C08G 18/36* (2013.01)

(58) Field of Classification Search
CPC .................................................. C08G 18/36
See application file for complete search history.

(56) References Cited

U.S. PATENT DOCUMENTS

| | | | | |
|---|---|---|---|---|
| 5,324,846 | A * | 6/1994 | Hirshman et al. | 554/121 |
| 5,380,886 | A * | 1/1995 | Daute et al. | 549/539 |
| 6,107,433 | A * | 8/2000 | Petrovic et al. | 528/1 |
| 2007/0232816 | A1 | 10/2007 | Soi et al. | |
| 2010/0240860 | A1* | 9/2010 | Abraham et al. | 528/361 |
| 2013/0090449 | A1* | 4/2013 | Whitehouse | 528/60 |

FOREIGN PATENT DOCUMENTS

| | | |
|---|---|---|
| JP | H04-163451 | 6/1992 |
| JP | H04-364195 | 12/1992 |
| JP | H09-222707 | 8/1997 |
| JP | H10-319551 | 12/1998 |
| JP | 2007-56157 | 3/2007 |
| WO | WO 03/093215 A1 | 11/2003 |
| WO | WO 2005-090501 | 9/2005 |
| WO | WO 2009/058367 | 5/2009 |
| WO | WO 2011/029738 A1 * | 4/2011 |

OTHER PUBLICATIONS

Derwent Abstract of JP 2010-069377A Apr. 2, 2010.*
International Search Report for corresponding International Application No. PCT/FR2010/051894, dated Jan. 24, 2011.

* cited by examiner

*Primary Examiner* — Jeffrey Washville
(74) *Attorney, Agent, or Firm* — Davidson, Davidson and Kappel, LLC

(57) ABSTRACT

The present invention relates to a method for preparing polyols of formula (I")

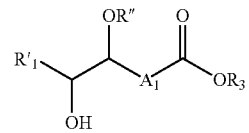

$R'_1$ being H or an alkyl group, R" being especially an alkyl group, $A_1$, being an alkylene radical and $R_3$, are being especially a group $-A_2-O-Y'$, $A_2$ being an alkylene radical and Y' being especially H,
said method especially comprising a step of epoxidation of a compound of formula

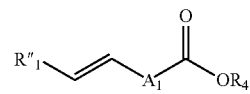

$R''_1$ being H or an alkyl group, $A_1$ being defined as above in formula (I") and
$R_4$ being especially a group $-A_2-O-Y_1'$, $A_2$ being defined as above in formula (I") and $Y'_1$ being especially H,
in order to obtain a compound of formula

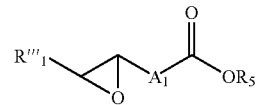

$A_1$ being defined as above, $R'''_1$ being H or an alkyl group and $R_5$ being especially a group of formula $-A_2-O-Y'_2$, $A_2$ being as defined above in formula (I") and $Y'_2$ being especially H.

12 Claims, No Drawings

METHOD FOR PREPARING POLYOLS AND PRODUCTS OBTAINED

This application is a national phase application under 35 U.S.C. §371 of International Application No. PCT/FR2010/051894 filed on Sep. 10, 2010, which claims priority to French Application No. 0956260, filed on Sep. 11, 2009, the disclosures of which are all hereby incorporated by reference herein.

The present invention relates to a novel method for preparing polyols, notably diols as well as the novel polyols obtained.

BACKGROUND

There exist different approaches for synthesizing polymers from vegetable oils. The first, the most widespread consists of considering triglycerides as base materials, the latter being able to be epoxidized and then for example alcoholized or hydro formulated, in order to make them functionable and polymerizable.

An oil is a mixture of triglycerides (triesters) formed by condensation of fatty acids and of glycerol. The high number of types of fatty acids (up to 24) present in each fat and the multiple possibilities of their combinations with glycerol molecules ensure that fats are highly complex mixtures of compounds, the properties of which vary from one oil to another. The nature of the triglycerides may therefore vary within a same oil.

The reactive sites present in a triglyceride are mainly double bonds and ester functions. The reactivity of double bonds allows the introduction of hydroxyl functions, thereby allowing access to multihydroxlated monomers. It is nevertheless impossible to obtain triglycerides having perfectly defined structures and functionalities.

The synthesis of polyols from vegetable oil is well described in the literature since the latter are excellent precursors for synthesizing polymers. These materials have one popularity because of the natural origin of the precursors and of the attractive properties provided by the structure and the composition of the vegetable oils. The reactive sites in all fats are ester functions and double bonds. Certain oils also have other groups such as hydroxyls or epoxides.

The double bonds of these compounds are generally not sufficiently reactive for being used as sites of radical polymerization. Nevertheless, at a high temperature (330° C.), the double bonds may migrate along the backbone in order to form conjugate sites, which facilitates condensations of the Diels-Alder type. Oligomers were synthesized by vulcanization of oils with sulfur monochloride and used as additives in the gum industry for example. Oligomers were also synthesized by cationic polymerization in the presence of boron trifluoride (Croston et al., *J. Amer. Oil Chem. Soc.* 1952, 331-333), for application in the formulations of inks. Other reactions involving double bonds, such as polymerization by metathesis gave the possibility of obtaining oligomers (Refvik et al., *J. Amer. Oil Chem. Soc.* 1999, 76, 93-98) and the materials which stem from this are rarely utilizable because they are very poorly defined.

It is therefore necessary to better control functionalization of the vegetable oils.

As already indicated, the presence of double bonds on the backbone allows introduction of hydroxyl groups. The latter may be achieved by direct oxidation of the double bonds, which consists of having an oxygen screen pass through the oil heated to 135° C. (G., Soucek et al. "Spectroscopic investigation of blowing process of soybean oil", Surface Coatings International, Part B, Coatings Transactions. 2003, 86: 221-229). Control of the oxidation is not satisfactory and many byproducts are formed such as peroxides, aldehydes, ketones, splittings of chains, etc. The only advantage of these polyols is their low price cost and their synthesis is achieved in a single step, in spite of the many treatments applied to the final product (odors, high acid index, dark color, etc.).

An organometal catalyst may also be used in order to better control the oxidation reaction (WO2006/094227; WO2007/143135) in the presence of an oxidant.

Polyols having primary hydroxyls may be prepared by hydro formulation of the unsaturations (Guo et al., *J. of Polymers and the Environment.* 2002, 10: 49-52). This method involves a reaction between carbon monoxide and dihydrogen, causing the formation of an aldehyde group which is converted into a hydroxyl by hydrogenation. Rhodium-based catalysts generally used are very efficient (conversions close to 100%) but also very costly. Conversely, cobalt-based catalysts are inexpensive but less efficient. By ozonolysis of the double bonds, it is also possible to obtain polyols having terminal hydroxyl groups (Guo et al., *J. of Polymer Sci.,* 2000, 38: 3900-3910). The ozone passes through a solution of vegetable oil and ethylene glycol, in the presence of an alkaline catalyst.

Another route for accessing polyols consists of conducting a preliminary reaction of epoxidation of the unsaturations. Many studies described in the literature describe the epoxidation of fats (Swern, et al. *J. Am. Chem. Soc.* 1944, 66, 1925-1927; Findley et al., *J. Am. Chem. Soc.* 1945, 67, 412-414: U.S. Pat. No. 5,026,881; U.S. Pat. No. 3,328,430; Petrović et al., *Eur. J. Lipid Sci. Technol.* 2002, 104: 293-299 and U.S. Pat. No. 4,647,678). Petrovic recently demonstrated the possibility of achieving epoxidation of vegetable oil via an enzymatic route (Vicek, T. et al., *J. Amer. Oil Chem. Soc.* 2006, 83: 247-252) or catalyzed with an ion exchange resin (Sinadinović-Fiser et al., J. Amer. Oil Chem. Soc. 2001, 78: 725). Nevertheless the most common route is the use of a peracid formed in situ, generally hydrogen peroxide in the presence of a carboxylic acid (most often formic acid in a catalytic amount). The reaction is conducted between 50 and 80° C. for 1 to 4 hours.

It is important to emphasize that the epoxidation of fats already having a primary alcohol at the end of the chain was never achieved from a peracid formed in situ. This reaction cannot be conducted under the same conditions as previously because of secondary reactions between the carboxylic acid and the terminal alcohol.

The epoxidized vegetable oils were used as intermediates in many syntheses. The Petrovic group describes the opening of the epoxides with alcohols, inorganic acids and by hydrogenation under acid catalyses (Guo et al., *J. Polym. Sci. Part A: Polym. Chem.* 2000, 38: 3900-3910). Epoxidized triglycerides were modified by reaction with HCl or HBr in the presence of acetone (solvent) by hydrogenation with $H_2$ in the presence of isopropanol and of Raney nickel as a catalyst, and finally by methanol in the presence of isopropanol and of an acid catalyst (for example fluoboric acid).

These functional triglycerides have different reactivities: the one derived from the opening with methanol being the most reactive towards isocyanates for the chemistry of polyurethanes. Petrovic increases the reactivity of the polyols obtained by ethoxylation (opening of ethylene oxide by the secondary alcohol under acid catalyses), which converts the secondary alcohols into primary alcohols. However it is noted that the use of an acid catalyst causes secondary reactions, such as the formation of a methyl ester during the opening of the epoxide with methanol. The solution lies in the use of a specific catalyst for opening the epoxide and operating at lower temperatures in order to avoid secondary coupling reactions. Finally, it is interesting to note that the US Patent Application, published under number 2006/7045577, describes the synthesis of polyurethane from soya bean oil according to a two-step process: (i) the oil is epoxidized from conventional methods using a peracid and (ii) the epoxidized soya bean oil reacts with carbon dioxide in order to give a carbonated vegetable oil. The reaction of this product with a diamine allows access to a polyurethane without using any isocyanates.

SUMMARY OF THE INVENTION

The object of the present invention is to provide a method for preparing polyols from vegetable oil esters giving the possibility of getting rid of the aforementioned drawbacks.

The object of the present invention is also to provide a method for preparing polyols comprising the use of catalysts better meeting environmental expectations than most homogeneous catalysts used and which limit the secondary reactions.

The object of the present invention is also to provide a method which, unlike the method of the prior art which relate to the chemical transformation from triglycerides having poorly defined structures, consists in a simple and efficient route for chemical modification of monoesters or of triglycerides in order to obtain functional precursors with controlled functionality.

The object of the present invention is to provide a simple preparation method in three steps via mono- or di-esters of vegetable oil.

An object of the present invention is to provide a three step method allowing access to novel synthons, mono-esters of di-esters, all at least bifunctional (polyols) and having well defined structures and requiring a specific catalyse.

The present invention relates to a method for preparing a polyol fitting the following general formula (I"):

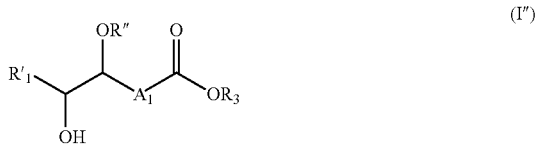

(I")

wherein:
R'$_1$ represents H or a linear or branched alkyl group comprising from 2 to 14 carbon atoms, said alkyl group may optionally be substituted with one or more OR$_a$ groups, R$_a$ representing H or a group R' as defined below,
A$_1$ represents a linear or branched divalent alkylene radical, comprising from 2 to 14 carbon atoms,
R" represents:
  a linear or branched alkyl group R', comprising from 1 to 18 carbon atoms, or
  a group of formula -A$_2$-OH, A$_2$ representing a linear or branched divalent alkylene radical, comprising from 1 to 10 carbon atoms, if necessary comprising one or more substituents, notably selected from the group formed by the phenylene radical and the radical of formula —(CH$_2$OCH$_2$)$_n$—, n representing an integer comprised between 1 to 100, preferably from 6 to 50, and preferably equal to 6, 13 or 45,
A$_2$ preferably representing a radical of formula —CH$_2$-A$_3$-CH$_2$—, A$_3$ representing a group of formula —(CH$_2$OCH$_2$)$_n$—, n representing an integer comprised between from 1 to 100, and preferably equal to 6, 13 or 45, or a phenylene radical,
R$_3$ represents:
  a linear or branched alkyl group R$_2$, comprising from 1 to 10, preferably from 1 to 6 carbon atoms, or
  a group of formula -A$_2$-O—Y', A$_2$ being as defined as above and Y' representing a hydrogen atom or a group of formula (A')

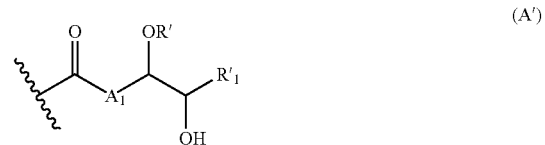

(A')

A$_1$, R' and R'$_1$ being as defined above in formula (I"),
it being understood that when R" is a group R' then R$_3$ represents a group of formula -A$_2$-O—Y', and when R" is a group -A$_2$-OH then R$_3$ represents a group R$_2$,
said method comprising the following steps:
a) a step for epoxidation of the compound of the following formula (IV"):

(IV")

A$_1$ being as defined above in formula (I"),
R"$_1$ representing H or a linear or branched alkyl group, comprising from 2 to 14 carbon atoms, said alkyl group may optionally contain one or 2 double bonds, and said alkyl group may also if necessary be substituted with an OH group,
R$_4$ representing an alkyl group R$_2$ as defined above, or a group of formula -A$_2$-O—Y$_1$', A$_2$ being as defined above and Y'$_1$ representing a hydrogen atom or a group of formula (A'$_1$)

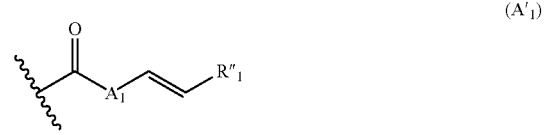

(A'$_1$)

A$_1$ being as defined above in formula (I") and R"$_1$ being as defined above in formula (IV"),
in order to obtain a compound of the following formula (V"):

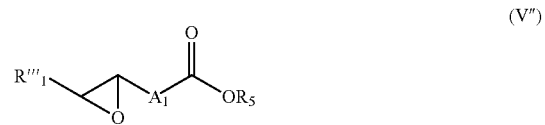

(V")

$A_1$ being as defined above in formula (I"), $R'''_1$ representing H or a linear or branched alkyl group, comprising from 2 to 14 carbon atoms, said alkyl group may optionally contain one or two epoxide groups, and said alkyl group may also if necessary be substituted with an OH group, $R_5$ representing an alkyl group $R_2$ as defined above, or a group of formula $-A_2-O-Y'_2$, $A_2$ being as defined above and $Y'_2$ representing a hydrogen atom or a group of formula ($A'_2$)

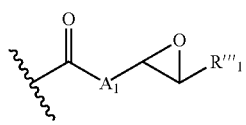

(A'$_2$)

$A_1$ being as defined above in formula (I") and $R'''_1$ being as defined above in formula (V"), and b) a step for opening the epoxide ring of the compound of formula (V") with an alcohol of formula R"OH, R" being as defined above, in order to obtain a compound of formula (") as defined above, and c) a step for recovering the compound of formula (I") as defined above.

The initial compound of formula (IV") encompasses both the compounds (IV') and (IV"-1):

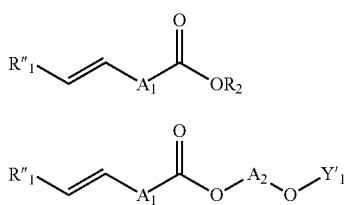

(IV"-1)

(IV')

The compound (IV"-1) is obtained by transesterification of a vegetable oil, notably sunflower, rape seed or castor oil, with an alcohol $R_2OH$, and the compound (IV') is obtained by transesterification of the compound (IV"-1) with a diol HO-$A_2$-OH.

When the epoxidation step a) is carried out on a compound (IV"-1), a compound (V"-1) is then obtained:

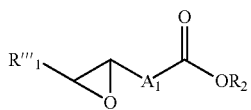

When the epoxidation step a) is carried out on a compound (IV'), a compound (V") is then obtained:

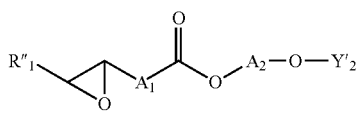

When the step for opening the ring b) is carried out on a compound (V"-1), a compound (I"-1) is then obtained:

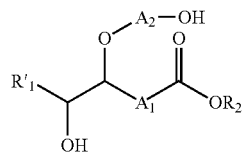

The compound for formula (I"-1) is a compound of the monoester type comprising at least two hydroxyl functions. It may optionally contain other hydroxyl functions depending on the nature of $R'_1$.

When the step for opening the ring b) is carried out on a compound (V'), a compound (I') is then obtained:

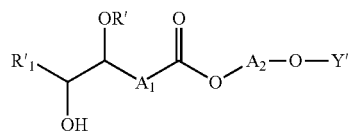

The compound of formula (I') is a compound of the monoester or diester type (depending on the nature of Y') comprising at least two hydroxyl functions. It may optionally contain other hydroxyl functions depending on the nature of $R'_1$.

The initial product (IV") contains a group $R"_1$ which may optionally contain one or two double bonds. Thus, during the epoxidation step leading to the compound (V"), these double bonds may also be epoxidized whence the nature of the group $R'''_1$. Finally, during the step for opening the ring, the epoxide groups present in the group $R'''_1$ are then also modified, whence the aforementioned definition of $R'_1$ and therefore the optional presence of one or two hydroxyl groups in $R'_1$.

According to an embodiment, the method of the invention relates to a method for preparing a polyol fitting the following general formula (I"-1):

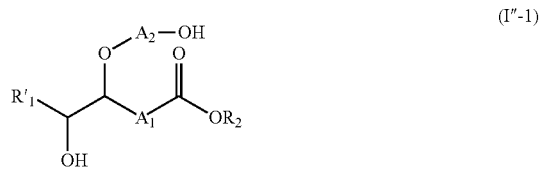

(I"-1)

wherein:

$R'_1$ represents H or a linear or branched alkyl group, comprising from 2 to 14 carbon atoms, said alkyl group may optionally be substituted with one or several $OR_a$ groups, $R_a$ representing H or a group R' as defined below, $A_1$ represents a linear or branched divalent alkylene radical comprising from 2 to 14 carbon atoms, $A_2$ represents a linear or branched divalent alkylene radical, comprising from 1 to 10 carbon atoms, if necessary comprising one or more substituents, notably selected from the group consisting of the phenylene radical and the radical of formula $-(CH_2OCH_2)_n-$, n representing an integer comprised between from 1 to 100, preferably from 6 to 50, and preferentially equal to 6, 13 or 45, $A_2$ preferably representing a radical of formula —$CH_2$-$A_3$-$CH_2$—, $A_3$ representing a group of formula —$(CH_2OCH_2)_n$—, n representing an integer comprised between from 1 to 100 and preferably equal to 6, 13 or 45, or a phenylene radical, $R_2$ represents a linear or branched alkyl group comprising from 1 to 10, preferably from 1 to 6 carbon atoms, said method comprising the following steps:

a) a step for epoxidation of a compound of the following formula (II'-1):

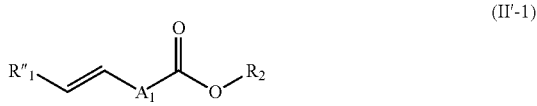

$R''_1$ representing H or a linear or branched alkyl group, comprising from 2 to 14 carbon atoms, said alkyl group may optionally contain one or two double bonds, and said alkyl group may also if necessary be substituted with an OH group, $A_1$ and $R_2$ being as defined above in formula (I''-1), in order to obtain a compound of the following formula (IV''-1):

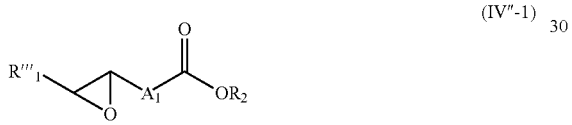

$A_1$ and $R_2$ being as defined above in formula (I''-1), $R'''_1$ representing H or a linear or branched alkyl group, comprising from 2 to 14 carbon atoms, said alkyl group may optionally contain one or two epoxide groups, and said alkyl group may also if necessary be substituted with an OH group, b) a step for opening the epoxide ring with a diol of formula HO-$A_2$-OH, $A_2$ being as defined above, in order to obtain a compound of formula (I''-1) as defined above, and c) a step for recovering the compound of formula (I''-1) as defined above.

According to another embodiment, the present invention relates to a method for preparing a polyol fitting the following general formula (I'):

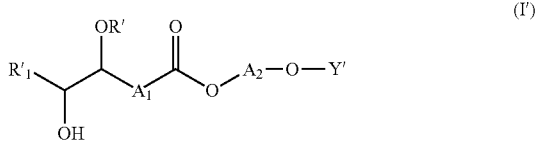

wherein:

$R'_1$ representing H or a linear or branched alkyl group, comprising from 2 to 14 carbon atoms, said alkyl group may optionally be substituted with one or more $OR_a$ groups, $R_a$ representing H or a group R' as defined below, R' represents a linear or branched alkyl group, comprising from 1 to 18 carbon atoms, $A_1$ represents a linear or branched divalent alkylene radical, comprising from 2 to 14 carbon atoms, $A_2$ represents a linear or branched divalent alkylene radical, comprising from 1 to 10 carbon atoms, if necessary comprising one or more substituents, notably selected from the group consisting of the phenylene radical and of the radical of formula —$(CH_2OCH_2)_n$—, n representing an integer comprised between from 1 to 100, preferably from 6 to 50, and preferentially equal to 6, 13 or 45, $A_2$ preferably representing a radical of formula —$CH_2$-$A_3$-$CH_2$—, $A_3$ representing a group of formula —$(CH_2OCH_2)_n$—, n representing an integer comprised from 1 to 100, and preferably equal to 6, 13 or 45, or a phenylene radical, Y' representing a hydrogen atom or a group of formula (A')

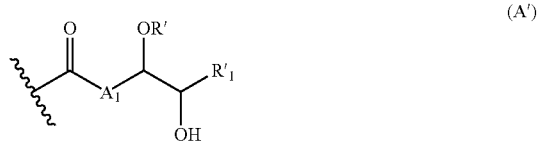

$A_1$, R' and $R'_1$ being as defined above in formula (I'), said method comprising the following steps:

a) a step for transesterification of a compound of the following formula (II'):

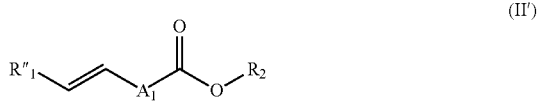

$R''_1$ representing H or a linear or branched alkyl group, comprising from 2 to 14 carbon atoms, said alkyl group may optionally contain one or two double bonds, and said alkyl group may also if necessary be substituted with an OH group, $A_1$ being as defined above in formula (I'), $R_2$ representing a linear or branched alkyl group, comprising from 1 to 10, preferably from 1 to 6 carbon atoms, with a diol of the following formula (III):

HO-$A_2$-OH    (III)

in order to obtain a compound of the following formula (IV'):

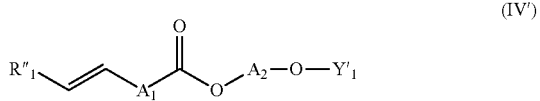

$A_1$, $A_2$ and $R''_1$ being as defined above, $Y'_1$ representing a hydrogen atom or a group of formula ($A'_1$)

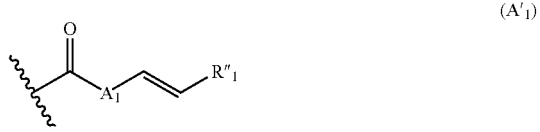

$A_1$ being as defined above in formula (I') and $R''_1$ being as defined above in formula (II'), b) a step for epoxidation of the compound of the aforementioned formula (IV') in order to obtain a compound of the following formula (V"):

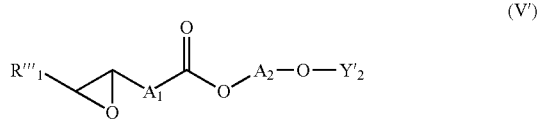
(V')

$A_1$ and $A_2$ being as defined above in formula (I'), $R'''_1$ representing H or a linear or branched alkyl group, comprising from 2 to 14 carbon atoms, said alkyl group may optionally contain one or two epoxide groups, and said alkyl group may also if necessary be substituted with an OH group, $Y'_2$ representing a hydrogen atom or a group of formula $(A'_2)$

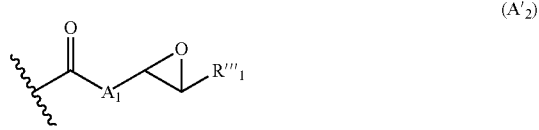
(A'$_2$)

$A_1$ being as defined above in formula (I') and $R'''_1$ being as defined above in formula (V'), c) a step for opening the epoxide ring with an alcohol of formula R'OH, R' being as defined above, in order to obtain a compound of formula (I') as defined above, and d) a step for recovering the compound of formula (I') as defined above.

Thus, the method of the invention consists of synthesizing novel polymers from fatty acid mono-esters. The latter are generally obtained for example by transesterification of triglycerides with a short alcohol ($R_2OH$, $R_2$ being as defined above) preferably with methanol or ethanol.

These esters, and more particularly sunflower or castor methyl or ethyl esters, were therefore used as base 'synthons' in the present invention.

By using a variety of sunflower oil for which the oleic acid content is particularly high and by separating by fractionated distillations the different sunflower oil methyl esters, oleic acid methyl esters (a single double bond per fatty chain) of high purity are obtained. It is from this monofunctional precursor that it is then possible to provide a selected number of hydroxyl groups and thereby control the functionality of this monomeric 'synthon'. A well defined structure of such monomers is actually indispensable for elaborating polymeric materials having controlled and reproducible properties. As the desired polymers are linear, it was for example sought to create at least difunctional (di-OH) monomers from oleic sunflower methyl esters.

Within the scope of the present invention, the inventors focused on the use of catalysts better meeting the environmental expectations than most homogeneous catalysts used and which limit secondary reactions. In this sense, heterogeneous catalyses, notably the use of ion exchange resins is particularly of interest. Such resins are efficient catalysts for promoting many reactions such as esterifications, etherifications, transalkylations and alkylations (G. D. Yadav, P. H. Mehta, Indust. Eng. Chem. Res. 1994, 33: 2198-2208).

Heterogeneous catalyses also provides non-negligible advantages as compared with homogeneous catalyses (recycling, selectivity and non-toxicity). This novel method was then applied to the opening of epoxidized fats.

The method of the invention therefore contemplates several routes for obtaining polyols:

a route in three steps via monoesters in particular comprising the transesterification of vegetable oil methyl esters for forming mono esters, epoxidation and then opening of the rings; and a three step route via diesters in particular comprising the transesterification of vegetable oil methyl esters in order to form diesters, epoxidation and opening of rings.

The different reactions set into play for the first two methods are (i) the transesterification of the ester group with diols allowing the grafting of a first primary hydroxyl function (aforementioned step a)) (ii) epoxidation of the double bond (aforementioned step b)), followed by (iii) the opening of the epoxide providing the second hydroxyl function (aforementioned step c)).

Thus, the present invention allows preparation of polyols fitting one of the two following formulae:

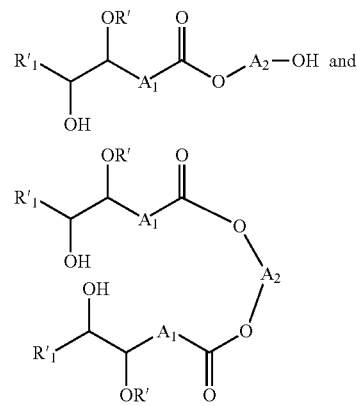

i.e., non-symmetrical diols with a primary OH function (at the end of the chain) and a secondary OH function on the one hand, and symmetrical diols with two secondary OH functions on the other hand.

More particularly, the aforementioned method relates to the preparation of diols. Thus, the present invention also relates to a method as defined above, for preparing a diol fitting the following general formula (I):

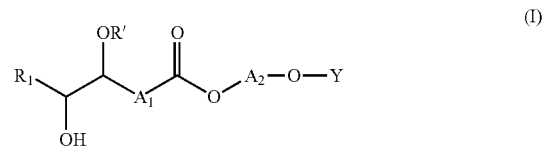
(I)

wherein:

$R_1$ representing H or a linear or branched alkyl group, comprising from 2 to 14 carbon atoms, R', $A_1$ and $A_2$ are as defined above in formula (I'),
Y represents a hydrogen atom or a group of formula (A)

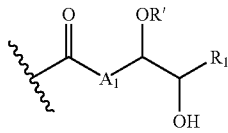
(A)

$A_1$, R' and $R_1$ are as defined above in formula (I'),
said method comprising the following steps:
a) a step for transesterification of a compound of the following formula (II):

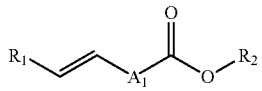
(II)

$R_1$ is as defined above and $R_2$ and $A_1$ are as defined above in formula (I') and (II'),
with a diol of the following formula (III):

(III)

in order to obtain a compound of the following formula (IV):

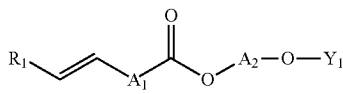
(IV)

$A_1$, $A_2$ and $R_1$ being as defined above in formula (I),
$Y_1$ representing a hydrogen atom or a group of formula ($A_1$)

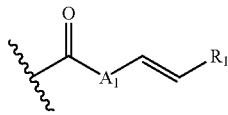
($A_1$)

$A_1$ being as defined above in formula (I) and $R_1$ being as defined above in formula (II),
b) a step for epoxidation of the compound of the aforementioned formula (IV) in order to obtain a compound of the following formula (V):

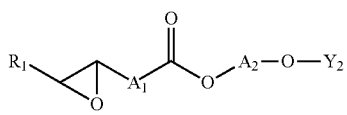
(V)

$A_1$, $A_2$ and $R_1$ being as defined above in formula (I),
$Y_2$ representing a hydrogen atom or a group of formula ($A_2$)

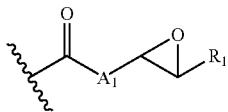
($A_2$)

$A_1$ being as defined above in formula (I) and $R_1$ being as defined above in formula (II),
c) a step for opening the epoxide cycle with an alcohol of formula R'OH, R' being as defined above, in order to obtain a compound of formula (I) as defined above, and
d) a step for recovering the compound of formula (I) as defined above.

The present invention also relates to a method as defined above, for preparing a diol fitting the general formula (I''-2):

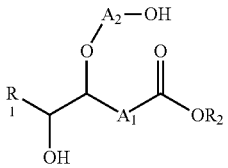
(I''-2)

wherein:
$R_1$ represents H or a linear or branched alkyl group, comprising from 2 to 14 carbon atoms,
$R_2$, $A_1$ and $A_2$ are as defined above in formula (I''-1), said method comprising the following steps:
a) a step for epoxidation of the compound of formula (II'-2):

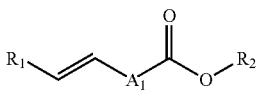
(II'-2)

$A_1$, $R_1$ and $R_2$ being as defined above in formula (I''-2),
in order to obtain a compound of the following formula (IV''-2):

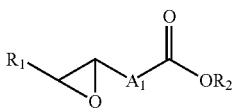
(IV''-2)

$A_1$, $R_1$ and $R_2$ are as defined above,
b) a step for opening the epoxide ring of the compound of formula (IV''-2) as defined above with a diol of formula HO-$A_2$-OH, $A_2$ being as defined above, in order to obtain a compound of formula (I''-2) as defined above, and
c) a step for recovering the compound of formula (I''-2) as defined above.

As indicated earlier, the diols of the invention of formula (I) and (I''-2) have the particularity of being derived from natural fats and of having an exact functionality of two.

The method of the invention for preparing the compounds (I) and I') comprises a first transesterification step carried out in heterogeneous catalyses (magnesium oxide or another heterogeneous catalyst) and preferably in the absence of any solvent (clean synthesis).

The second step of the method of the invention for preparing the compounds (I) and (I') is an epoxidation and this synthesis is peculiar because of the presence of the terminal hydroxyl group of the monoesters. Epoxidation requires the use of a peracid already formed in order to avoid a secondary reaction with the alcohol at the end of the chain and the opening of the epoxide is only possible under relatively mild conditions for inhibiting the formation of couplings. The specificity of this second step consists in the use of preformed peracid.

Finally, the third step of the method of the invention for preparing the compounds (I) and (I') consists of opening the epoxide with alcohols (methanol, ethanol, propanol, etc.) under acid catalyses. The specificity of this step consists in that it preferably applies a recyclable and selective ion exchange resin and is preferentially carried out in the absence of any solvent. It is also important to note that these three reactions follow each other without any intermediate purification (a single purification may be carried out at the end, which facilitates the setting up of the method).

Preferably, the method of the invention allows preparation of a diol fitting the following formula (I-1):

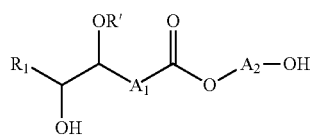

(I-1)

$A_1$, $A_2$, $R_1$ and R' being as defined above in formula (I).

The diol of formula (I-1) corresponds to a compound of formula (I) in which Y is a hydrogen atom. This diol comprises a primary OH function (at the end of the chain) and a secondary OH function.

The present invention also relates to a method for preparing a diol as defined above, said diol fitting the following formula (I-2):

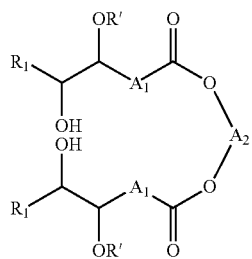

(I-2)

$A_1$, $A_2$, $R_1$ and R' are as defined above in formula (I).

The diol of formula (I-2) corresponds to a compound of formula (I) in which Y is a group of formula (A). This diol comprises two secondary OH functions.

According to a preferred embodiment, the step a) of the method of the invention is carried out in the presence of a catalyst selected from the group consisting of magnesium oxide, zinc acetate and sodium methanolate.

Preferably, said step a) is carried out at a temperature comprised between from 150 to 200° C. under nitrogen flow. This temperature range is selected depending on the nature of the catalyst used. For example, if the temperature is above 200° C., the catalyst is degraded.

According to a preferred embodiment, this step a) as defined above is carried out without any solvent, which is very advantageous in terms of ecology.

The present invention also relates to a method for preparing a diol as defined above, characterized in that the product of formula (IV) obtained at the end of step a) is in the form of a mixture of monoesters and diesters, the monoesters fitting the following formula (IV-1):

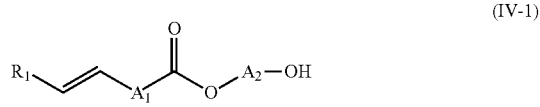

(IV-1)

and the diesters fitting the following formula (IV-2):

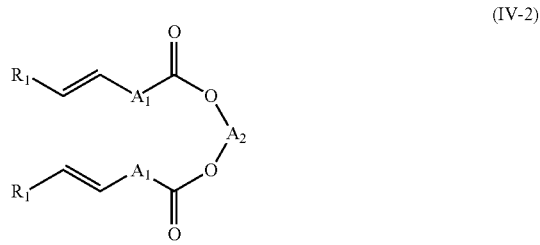

(IV-2)

$A_1$, $A_2$ and $R_1$ being as defined above in formula (I).

The monoester of formula (IV-1) corresponds to a compound of formula (IV) wherein $Y_1$ is H and the diester of formula (IV-2) corresponds to a formula (IV) in which $Y_1$ is a group of formula ($A_1$).

Within the scope of the method of the present invention, if the diol, i.e. the compound of formula (III) is used in a large excess (for example at a molar ratio of 100) (ratio between the number of moles of the diol (III) and the number of moles of the compound of formula (II)) up to 95% by weight of monoester (compound of formula (IV-1)), is obtained, while when the diol is used in default relatively to the compound of formula (II) (for example with a molar ratio of 0.5), up to 85% by weight of diester (compound of formula (IV-2)) is obtained. With the method of the invention it is therefore possible to control the composition of the obtained compound (monoester, diester or mixture) by suitably selecting the amounts of the initial products.

The present invention also relates to a method for preparing a diol as defined above, characterized in that the product of formula (V) obtained at the end of step b) is in the form of a mixture of monoesters and of diesters, the monoesters fitting the following formula (V-1):

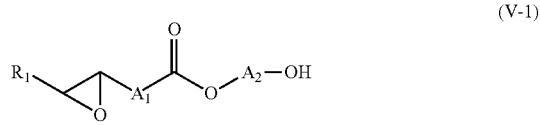

(V-1)

and the diesters fitting the following formula (V-2):

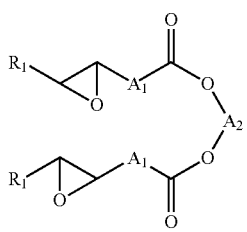 (V-2)

$A_1$, $A_2$ and $R_1$ are as defined above in formula (I).

The monoester of formula (V-1) corresponds to a compound of formula (V) in which $Y_2$ is H and the diester of formula (V-2) corresponds to a compound of formula (V) in which $Y_2$ is a group of formula ($A_2$).

The aforementioned method according to the invention may also comprise an intermediate step between step a) and step b) which consists of purifying the compounds of formula (IV), notably on a silica column or by distillation in a high vacuum.

For example, the monoester of formula (IV-1) is purified by using a heptane/acetone/petroleum ether 80/10/10 mixture and the diester of formula (IV-2) is purified by using a heptane/petroleum ether 80/20 mixture.

According to a preferred embodiment, the step b) of the method of the invention is carried out in the presence of a peracid, this step being notably carried out in vacuo at 200° C. for less than 3 minutes.

Among the peracids, mention may notably be made of metachloroperbenzoic acid (m-CPBA) and magnesium monoperoxyphthalate hexahydrate (MMPP).

The present invention also relates to a method for preparing a diol as defined above, in which, when the compound of formula (IV) is a compound in which $Y_2$ is a group of formula ($A_2$), the epoxidation step b) is carried out in the presence of $H_2O_2$ and of formic acid or in the presence of $H_2O_2$ and acetic acid.

The aforementioned method according to the invention may also comprise an intermediate step between step b) and step c) which consists of purifying the compounds of formula (V), notably on a silica column.

However, this purification step is optional, given that the compounds of formula (V) may also be used directly without being purified.

For example, the monoester of formula (V-1) is purified by using a toluene/ethyl acetate 60/40 mixture and the diester of formula (V-2) is purified by using a toluene/ethyl acetate 95/5 mixture.

According to a preferred embodiment, the preparation method according to the invention is characterized in that step c) is carried out in the presence of a catalyst selected from the group consisting of an acid catalyst of the proton ion exchange resin type, notably with sulfonic acid functions (resin Amberlyst® 15 Dry), heterogeneous catalysts, of para-toluenesulfonic acid (PTSA) or of methanesulfonic acid (MSA) at a temperature comprised between from 20° C. to 120° C., preferably at 70° C.

The aforementioned method according to the invention may also comprise an additional step consisting, at the end of step c) of purifying the compounds of formula (I), notably on a silica column.

However, this purification step is optional given that the compounds of formula (I) may also be used directly without being purified.

For example, the compounds of formula (I) are purified by using a toluene/ethyl acetate 40/60 mixture.

DETAILED DESCRIPTION

1. Step a): Reaction of Transesterification of the Compounds of Formula (II') or (II)

Within the scope of the method of the invention, this transesterification is carried out preferably from an ester of a light alcohol (notably methanol or ethanol . . . ) of oleic sunflower oil (compound of formula (II) or (II')) and from a diol (compound of formula (III) or (III')) notably in the presence of magnesium oxide as a catalyst. Several syntheses are carried out with different diols in order to modulate the properties of the monomers and therefore of the resulting polymers. Transesterifications were therefore carried out from propanediol, hexanediol, butanediol and hydroxyl telechelic poly(ethyleneoxide).

The reaction takes place between 150° C. and 200° C. under nitrogen flow. The progression of the reaction is tracked by different analyses and notably MNR (disappearance of the singlet of the methyl group). Depending on the reaction conditions, two products are obtained:

If the diol used is placed in a great excess, in majority at least 80%, or even 95% of monoesters (or derivatives of monoglycerides) are obtained having a terminal hydroxyl group. This alcohol at the end of the chain then provides a first functionality to the monomer.

Conversely, if the diol is voluntarily introduced in default, in majority at least 60%, or even 85% of diesters (or derivatives of diglycerides) are obtained. This second precursor then exactly has two double bonds through which will be introduced the hydroxyl groups, allowing access to monomers with a functionality equal to two.

| Alcohols used (II) or (II') | Reaction time | | Yield | |
|---|---|---|---|---|
| | Synthesis of monoesters | Synthesis of diesters | Synthesis of monoesters | Synthesis of diesters |
| Propanediol | 10 h | 15 h | 80% | 62% |
| Hexanediol | 10 h | 15 h | 80% | 60% |
| Polyoxyethylene ($M_w$ = 300 g/mol) | 15 h | 20 h | 75% | 59% |
| Polyoxyethylene ($M_w$ = 600 g/mol) | 15 h | 20 h | 75% | 59% |

Step a) (with $R_1$=$C_6H_{13}$; $A_1$=$C_9H_{18}$, $R_2$=$CH_3$; $A_2$=R) may thus notably be illustrated by the following diagram:

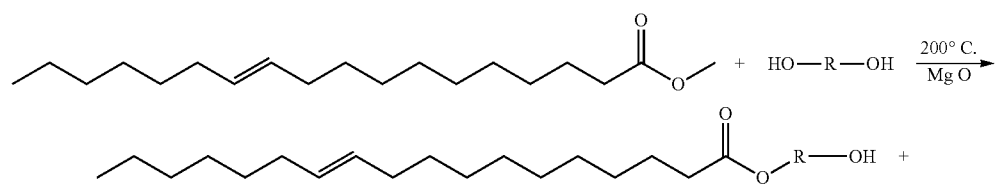

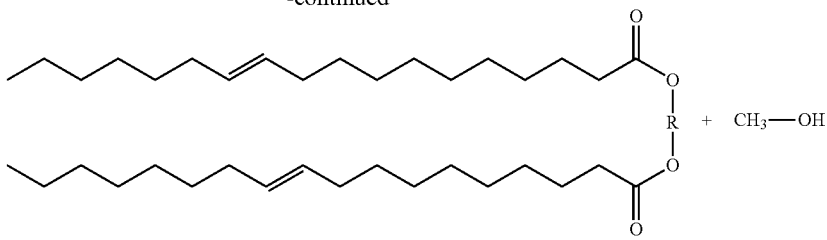

The prepared synthons (corresponding to the compounds of formula (IV)) are for example purified on a silica column with a heptane/acetone/petroleum ether 80/10/10 mixture for the monoester and a heptane/petroleum ether 80/20 mixture for the diester. The yields after purification are given in the table above.

At the end of this first step, two precursors are available: the first is a monoester (compound of formula (IV-1)) having a terminal hydroxyl group and a double bond on the chain; the second one is a diester (compound of formula (IV-2)) exactly having two double bonds in order to obtain subsequently a symmetrical polyol containing two hydroxyl groups. The synthesis route set into play is <<clean>> since it resorts to heterogeneous catalyses (magnesium oxide) and the synthesis takes place without any solvent. Industrial purification may be accomplished by distillation under a high vacuum.

2. Step b): Epoxidation of the Derivatives of Monoesters and Diesters Obtained after Transesterification The epoxidation of fats having a primary alcohol at the end of the chain by peracids formed in situ has never been dealt with and cannot be achieved under the same conditions as those described earlier. The epoxidation reaction is actually subject to interference caused by a secondary oxidation reaction of the terminal alcohol of the oleic sunflower monoester so as to form a carboxylic acid. As the reagent is consumed by this secondary reaction, epoxidation is not achieved.

Thus, a secondary esterification reaction occurs between the catalyst (carboxylic acid) and the terminal alcohol of the monoester according to the following scheme (specific case with $R_1=C_8H_{17}$ and $A_1=C_7H_{14}$):

bridges in an acid medium at 70° C. Another epoxidation strategy without using any reactive carboxylic acid was therefore developed by the inventors.

The method applied within the scope of the method of the invention for the epoxidation of a monoester with a terminal hydroxyl group (compounds of form a (IV-1)) lies in the use of an already formed and marketable peracid, i.e. notably metachloroperbenzoic acid (m-CPBA), and therefore avoids the use of potentially toxic metals.

The mechanism of this reaction may be illustrated according to the scheme hereafter:

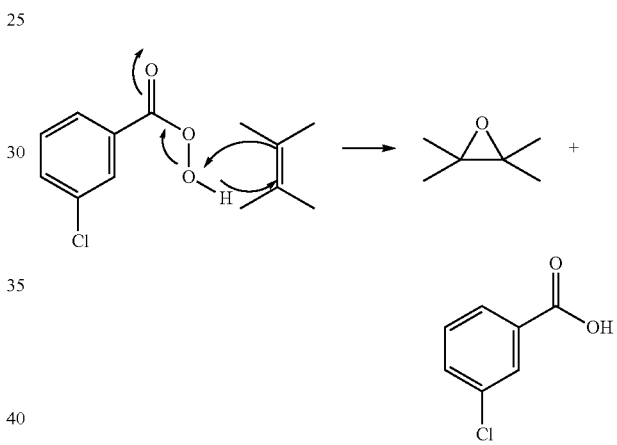

Within the scope of the invention, epoxidation was achieved with peracids (mCPBA, MMPP . . . ). The reaction may be tracked by MNR; the disappearance of the proton doublets of the double bond at 5.2 ppm as well as the appearance of a broad peak at 2.8 ppm allows tracking of the

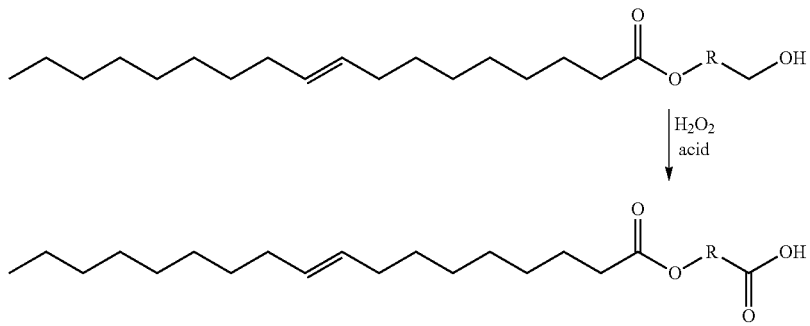

The reduction in the amount of catalyst or of the temperature in order to penalize the parasitic reaction nevertheless causes a significant increase in the reaction time, and in parallel an initial opening of the formed, fragile epoxide progression of the reaction. The conversion of the double bonds is total after 3 h. The excess m-CPBA is reduced into the corresponding carboxylic acid with a saturated solution of sodium sulfate. The organic phase is extracted with dichloromethane and then the residual carboxylic acid is transformed into sodiumchlorobenzoate (soluble in water) by means of two washings with a saturated solution of sodium bicarbonate.

The diesters (compounds of formula (IV-2)), not having any hydroxyl groups, may be epoxidized by using the standard procedure (H₂O₂+formic acid) or by using a peracid as indicated above, for example metachloroperbenzoic acid.

The obtained synthons are all purified on a silica column with a toluene/ethyl acetate 60/40 mixture for the epoxidized monoester and a toluene/ethyl acetate 95/5 mixture for the epoxidized diester.

3. Step c): Opening the Epoxides of the Monoesters and Diesters Epoxidized by Alcohols Within the scope of the present invention, the goal is to introduce hydroxyl groups on monoesters already having a terminal primary alcohol by opening the epoxides with an alcohol.

At 110° C. and under acid catalyses (p-toluenesulfonic acid), transesterification is favored as compared to the opening of the epoxide. Indeed, the primary alcohol at the end of the chain is set into play in these secondary reactions.

For example the formation of couplings is observed upon opening the epoxide notably according to the following scheme:

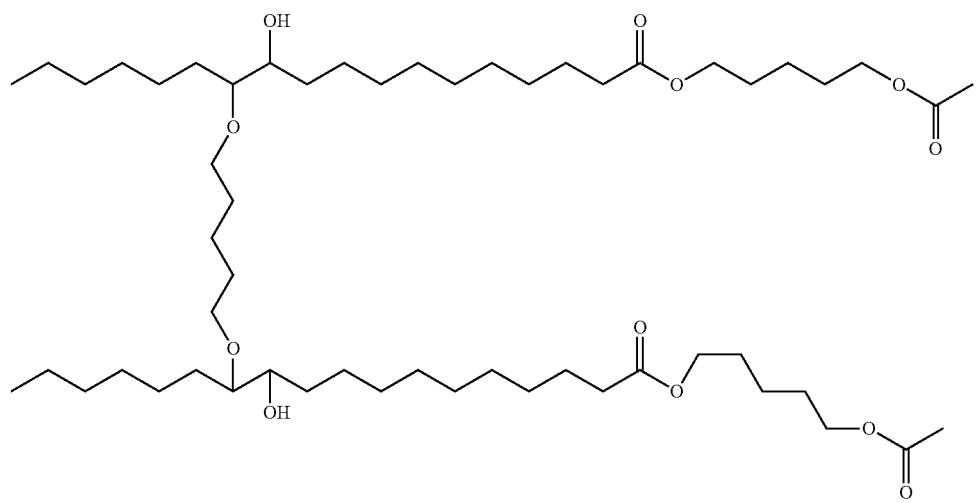

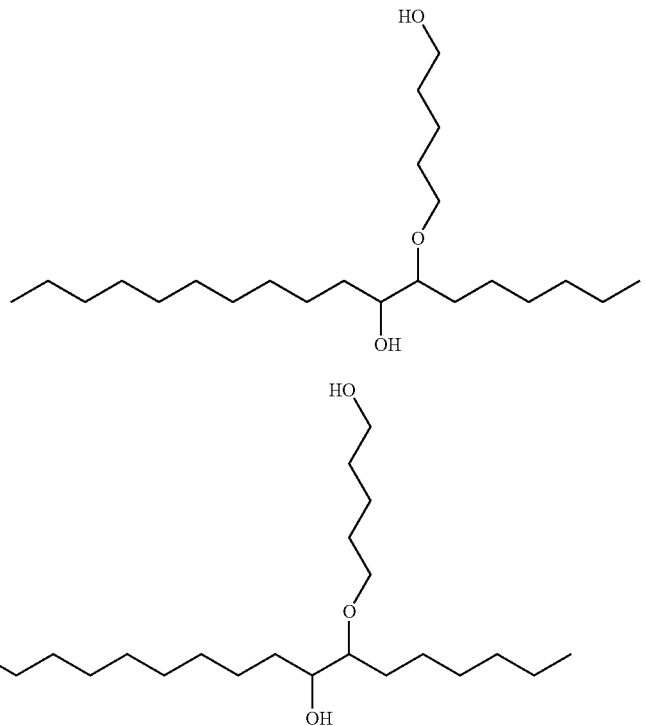

Tests conducted at lower temperatures show that the couplings are reduced but the opening of the epoxide is considerably slowed down. Many openings of epoxides use homogeneous acid catalysts (U.S. Pat. No. 4,508,853; Gruber et al., Fett Wissenschaft Technologie, 1987, 4:147-151; EP 0 260 499; U.S. Pat. No. 4,742,087; DE 4 232 167; Guo et al., J. Polym. Sci. A: Polym. Chem., 2000, 38: 3900-3910; U.S. Pat. No. 6,433,121; U.S. Pat. No. 6,573,354; Zlatanic et al., J. Polym. Sci. B: Polym. Physics, 2004, 42: 809-819; US 20070232816) or amines (DE 4 238 215).

The method of the present invention consists of using a specific catalyst upon opening the epoxide and operational at lower temperatures in order not to trigger a beginning of transesterification.

The reaction conditions applied for step c) of the method of the invention are milder than with conventional homogeneous catalyses (70° C. instead of 110° C.) and the synthesis is accomplished without any solvent. Thus, the epoxidized monoesters and diesters are mixed with a large excess of alcohol in the presence of 4% by mass of resin Amberlyst 15 Dry. The medium is heated to 70° C. for 15 h. The progression of the reaction is tracked by MNR by the disappearance of the peaks of the epoxide at 2.8 ppm. The mixture is then filtered in order to recover the catalyst.

The alcoholized synthons are then purified on a silica column with a toluene/ethyl acetate 40/60 mixture for the hydroxylated monoesters and diesters.

The present invention also relates to a compound fitting the following general formula (I"):

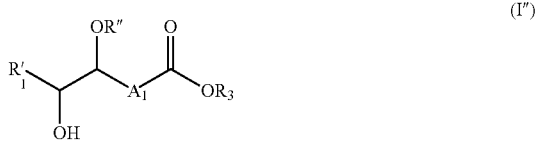

wherein:
$R'_1$ represents H or a linear or branched alkyl group, comprising from 2 to 14 carbon atoms, said alkyl group may optionally be substituted with one or more groups $OR_a$, $R_a$ representing H or a group R' as defined below,
$A_1$ represents a linear or branched divalent alkylene radical, comprising from 2 to 14 carbon atoms,
R" represents:
a linear or branched alkyl group R' comprising from 1 to 18 carbon atoms, or
a group of formula $-A_2$-OH, $A_2$ representing a linear or branched divalent alkylene radical, comprising from 1 to 10 carbon atoms, if necessary comprising one or more substituents, notably selected from the group consisting of the phenylene radical and of the radical of formula $-(CH_2OCH_2)_n-$ n representing an integer comprised from 1 to 100, preferably from 6 to 50, and preferentially equal to 6, 13 or 45,
$A_2$ preferably representing a radical of formula $-CH_2$-$A_3$-$CH_2-$, $A_3$ representing a group of formula $-(CH_2OCH_2)_n-$, n representing an integer comprised from 1 to 100, and preferably equal to 6, 13 or 45, or a phenylene radical, and
$R_3$ represents:
a linear or branched alkyl group $R_2$, comprising from 1 to 10, preferably from 1 to 6 carbon atoms, or
a group of formula $-A_2O-Y'$, $A_2$ being as defined above and Y' representing a hydrogen atom or a group of formula (A')

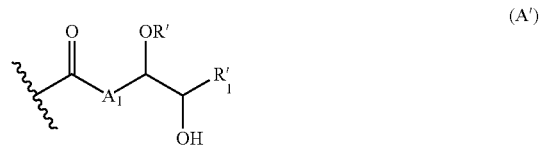

$A_1$, R' and $R'_1$ being as defined above in formula (I"),
it being understood that when R" is a group R' then $R_3$ represents a group of formula $-A_2-O-Y'$, and that when R" is a group $-A_2$-OH then $R_3$ represents a group $R_2$.

The present invention also relates to a compound fitting the following general formula (I"-1):

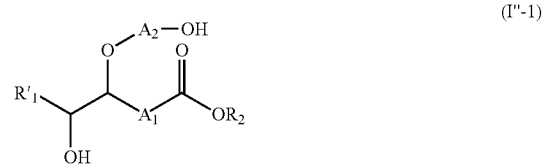

wherein:
$R'_1$ represents H or a linear or branched alkyl group, comprising from 2 to 14 carbon atoms, said alkyl group may optionally be substituted with one or more groups $OR_a$, $R_a$ representing H or a group R' as defined below,
$A_1$ represents a linear or branched divalent alkylene radical, comprising from 2 to 14 carbon atoms,
$A_2$ represents a linear or branched divalent alkylene radical, comprising from 1 to 10 carbon atoms, if necessary comprising one or more substituents, notably selected from the group consisting of the phenylene radical and of the radical of formula $-(CH_2OCH_2)_n-$,
n representing an integer comprised between from 1 to 100, preferably from 6 to 50, and preferentially equal to 6, 13 or 45,
$A_2$ preferably representing a radical of formula $-CH_2$-$A_3$-$CH_2-$, $A_3$ representing a group of formula $-(CH_2$ $OCH_2)_n-$, n representing an integer comprised from between 1 to 100, and preferably equal to 6, 13 or 45, or a phenylene radical, and
$R_2$ represents a linear or branched alkyl group, comprising from 1 to 10, preferably from 1 to 6 carbon atoms.

The present invention also relates to a compound fitting the following general formula (I'):

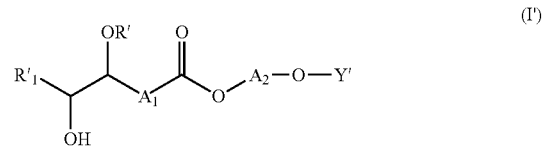

wherein:
$R'_1$ represents H or a linear or branched alkyl group, comprising from 2 to 14 carbon atoms, said alkyl group may optionally be substituted with one or more groups $OR_a$, $R_a$ representing H or a group R' as defined below,
R' represents a linear or branched alkyl group, comprising from 1 to 18 carbon atoms,
$A_1$ represents a linear or branched divalent alkylene radical, comprising from 2 to 14 carbon atoms, $A_2$ represents a linear or branched divalent alkylene radical, comprising from 1 to 10 carbon atoms, if necessary comprising one or more substituents, notably selected from the group consisting of the phenylene radical and of the radical of formula —$(CH_2OCH_2)_n$—, n representing an integer comprised between from 1 to 100, and preferably equal to 6, 13 or 45, Y' represents a hydrogen atom or a group of formula (A')

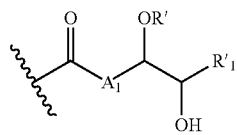

(A')

$A_1$, R' and $R'_1$ being as defined above in formula (I').

Among the aforementioned preferred compounds, mention may notably be made of the compounds of the following formula (I):

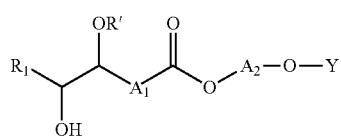

(I)

wherein:

$R_1$ represents a linear or branched alkyl group, comprising from 2 to 14 carbon atoms, and R', $A_1$ and $A_2$ are as defined above in formula (I'), and Y represents a hydrogen atom or a group of formula (A)

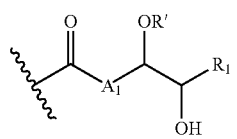

(A)

$A_1$, R' and $R_1$ are as defined above in formula (I).

Mention may also be made of other preferred compounds according to the present invention, fitting the following general formula (I-1):

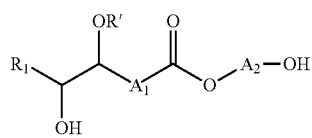

(I-1)

wherein:

$R_1$, R', $A_1$ and $A_2$ are as defined above in formula (I') and (I).

The present invention also relates to compounds fitting the following general formula (I"-1-1):

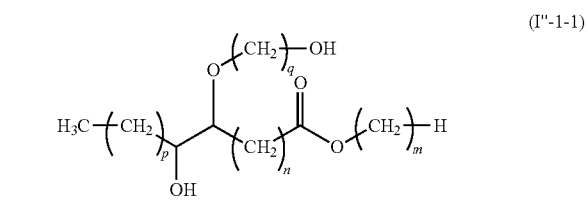

(I"-1-1)

wherein:

m, n, p and q are integers comprised between from 1 to 18, m being preferably equal to 2.

Preferably, in formula (I"-1-1), q is equal to 4.

The present invention also relates to compounds fitting the following general formula (I-1-1):

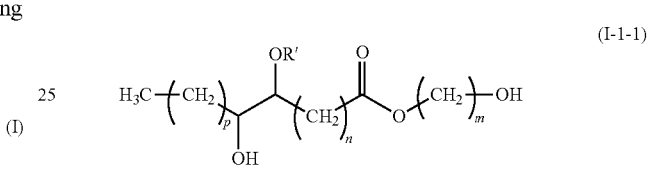

(I-1-1)

wherein:

m, n and p are integers comprised between from 1 to 18, and R' is as defined above in formula (I').

The present invention also relates to compounds fitting the following general formula (I-1-2):

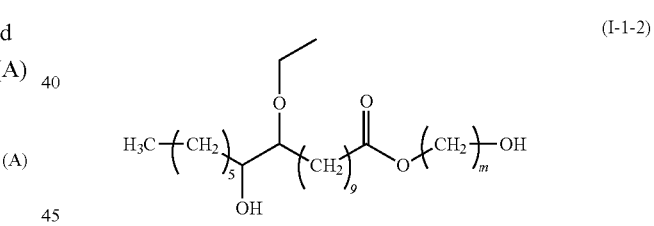

(I-1-2)

Another family of preferred compounds of the invention consists of the compounds fitting the following general formula (I-2):

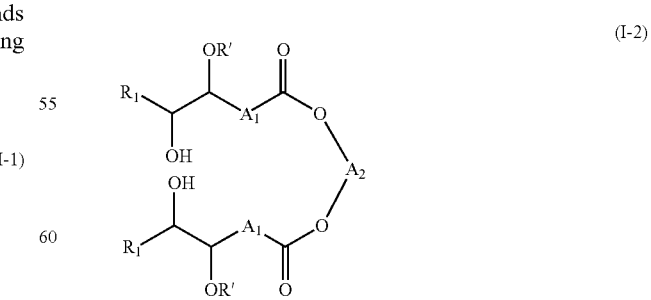

(I-2)

wherein:

$R_1$, R', $A_1$ and $A_2$ are as defined above in formulae (I') and (I).

Another family of preferred compounds of the invention consists of compounds fitting the following general formula (I-2-1):

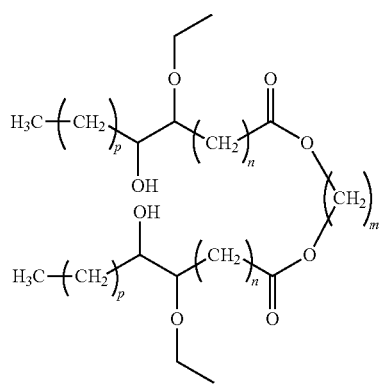
(I-2-1)

wherein:

m, n and p are integers comprised between from 1 to 18, and R' is as defined above in formula (I').

Another family of preferred compounds of the invention consists of the compounds fitting the following general formula (I-2-2):

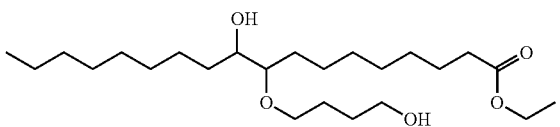
(I-2-2)

m being as defined above.

Among the preferred polyols of the invention, mention may notably be made of the two following specific compounds:

a diol (8) derived from sunflower oil:

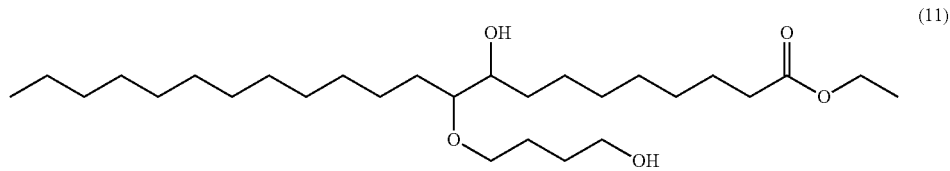 [SMILES: CCCCCCCCCCCCC(OCCCCO)C(O)CCCCCCCC(=O)OCC]
(8)

a diol (11) derived from rape seed oil:

(11)

The polyols according to the present invention, notably the diols, have the specificity of being well defined, with two primary or secondary hydroxyl groups. The derivatives of diesters are original because of their symmetry and the alcohol used for transesterification gives the possibility of varying the structure of the synthons and thus the properties of the resulting polymers.

The diols obtained by these different methods may then be used inter alia as monomers. Their purity allows optimization of the properties of the obtained polymers.

Thus, polyurethanes were then synthesized by bulk polymerization of these polyols with IPDI (or for example also with MDI, HMDI or HDI), at 60° C. in the presence of tin dibutyl dilaurate. Formation of the polyurethanes is confirmed by FTIR with the disappearance of the vibration band of the isocyanate. Steric exclusion chromatography confirms molar masses comprise between 14 000 and 50 000 g/mol. These di-OH monomers may also be used for the synthesis of other polymers such as polyesters, polyethers, polycarbonates, etc.

The polyol compounds according to the present invention of formula (I), (I') or (I") are notably used for reacting with polyisocyanates in order to form polyurethanes.

Thus, these compounds may be used for preparing rigid foams, of electric insulators, of coatings, of adhesives, of flexible foams (notably in the field of furniture or of automobiles) or of shoe soles.

More exactly, the polyols according to the present invention are used for preparing rigid foams by reacting them with polyisocyanates in the presence of a catalyst and of a foaming agent (to which may also be added surfactants, coloring agents, antioxidants, preservatives, plasticizers, cross-linking agents, flame retardants, etc.).

Preferably, such a rigid foam may be prepared by reacting together the following constituents: 60 g of polyisocyanate, 40 g of polyol, 1.2 g of water (foaming agent), 0.1-0.4 g of catalyst and 1-4 g of surfactant.

More exactly, the polyols according to the invention are used for preparing electric insulators by reacting them with polyisocyanates in the presence of an anti foaming agent and of a drying agent.

Preferably, such an electric insulator may be prepared by reacting together 60 g of polyol, 29 g of polyisocyanate, 0.6 g of anti foaming agent and 3 g of drying agent, and optionally 60 g of fillers (silica).

More exactly, the polyols according to the invention are used for preparing coatings by reacting them with polyisocyanates. For example, coatings are prepared by using pure polyols and polyisocyanates, or by using polyols and polyisocyanates with solvents (it is also possible to add coloring agents, pigments, fillers, flow additives, anti oxidants, bactericides, fungicides, corrosion inhibitors, catalysts or UV stabilizers).

For the preparation of adhesives according to the present invention, provision is also made for using pure polyols of the invention with pure polyisocyanates.

As regards flexible foams, preferably 60 g of polyol according to the invention, 100 g of isocyanate, 4.5 g of water (foaming agent), 0.12 g of catalyst 1, 0.38 g of catalyst 2 and 3 g of surfactant are used.

Finally, a specific formulation according to the invention for preparing shoe soles comprises 59 g of isocyanate, 94.5 g of polyol according to the invention, 4.1 g of ethylene glycol and 1.4 of catalyst.

The present invention also relates to the intermediate compounds fitting one of the following formulae:

(IV')

(IV)

(IV-1)

(IV-2)

(IV")

(IV"-1)

$R''_1$, $A_1$, $A_2$, $Y_1$, $Y'_1$, $R_2$, $R_4$ and $R_1$ are as defined above in formula (I), (I') and (I").

The present invention also relates to the intermediate compounds fitting one of the following formulae:

(V')

(V)

(V-1)

(V-2)

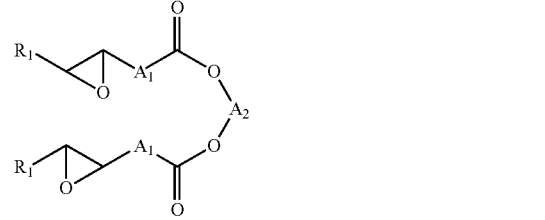

-continued

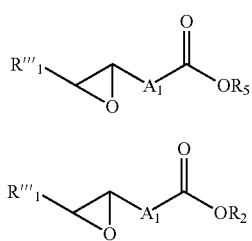
(V″)

(V″-1)

$R''_1$, $A_1$, $A_2$, $Y_2$, $Y'_2$, $R_5$, $R_2$ and $R_1$ are as defined above in formulae (I) and (I').

A particularly preferred family of intermediate compounds according to present invention consists of compounds fitting the following formula (V-3):

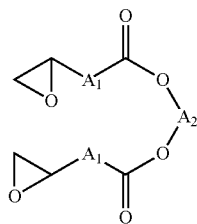
(V-3)

$A_1$ and $A_2$ are as defined above in formula (I'), and $A_1$ preferably representing a group $C_7H_{14}$.

The present invention therefore also relates to the synthesis of bis-epoxide precursors, notably for epoxy resins.

These bis-epoxide precursors have two terminal epoxide groups and are close to the structure of bisphenol A diclycidyl ether (BADGE). BADGE is widely used as a precursor in the synthesis of epoxy resin, by a condensation reaction with diamines. However BADGE is in the process of being banned because of the toxicity of its bisphenol A. The bis-epoxides according to the invention of the aforementioned formula (V-3) prove to be an alternative to the use of BADGE.

The literature already describes the use of vegetable oil in the formulation of epoxy resins: epoxidised sunflower oil (Jiang Zhu et al., *Journal of Applied Polymer Science*, 2004, 91, 3513-3518), epoxidized castor oil (Park et al., *Macromolecular Chemistry and Physics*, 2004, 205, 2048-2054) or carbonated soya bean oil (Parzuchowski et al., *Journal of Applied Polymer Science*, 2006, 102, 2904-2914). Nevertheless these oils only replace a small proportion of BADGE because of their low reactivity. The attained epoxy resins have equivalent mechanical properties or even superior to commercial epoxy resins from petroleum. For the moment, a maximum of 30% of epoxidized oil has been incorporated into commercial resins. With the mixture of epoxidized flax oil, of bisphenol F diglycidyl ether (BFDGE), and of an anhydride adjuvant, it is possible to obtain resins containing up to 70% of epoxidized flax oil (Miyagawa et al., *Marcomoecular Materials and Engineering*, 2004, 289, 629-635).

The synthesis of epoxy resins from 100% of vegetable oil is not possible because of the low reactivity of the internal epoxide groups in the chain. The synthesis route proposed within the scope of the present invention gives the possibility of obtaining precursors having two terminal epoxide groups, which increases the reactivity towards amines and allows the synthesis of epoxy resins from 100% of vegetable oil.

The method for preparing the compounds of formula (V-3) may be illustrated by the diagram hereafter:

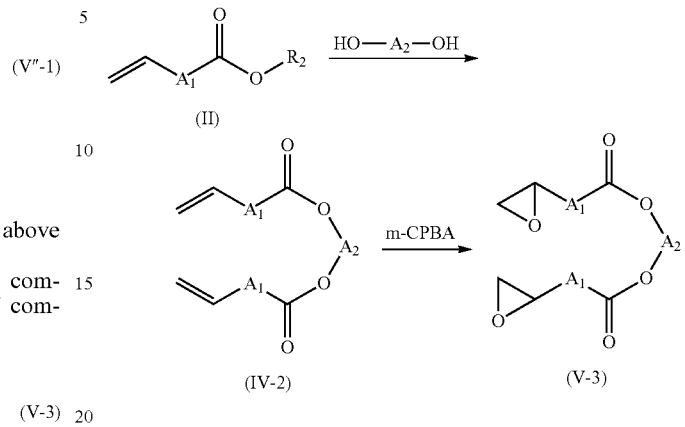

Preferably $A_1$ represents a radical $C_7H_{14}$.

The present invention also relates to polymers of the polyurethane type as obtained by polymerization of the polyols of the present invention, notably of formulae (I″), (I′) or (I), with (poly)isocyanates.

It also relates to polymers of the polyester type as obtained by polymerization of the polyols of the present invention, notably of formulae (I″), (I′) or (I).

EXPERIMENTAL PART

Example 1

Preparation of Oleic Sunflower Oil Ethyl Esters

This example relates to the preparation of the compound (1) of the following formula:

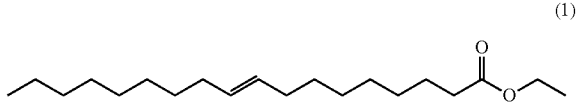 [SMILES: CCCCCCCC/C=C/CCCCCCCC(=O)OCC]
(1)

This is a compound of formula (II) in which $R_1$ represents an alkyl group comprising 8 carbon atoms, $A_1$ represents an alkylene radical comprising 7 carbon atoms and $R_2$ represents an ethyl group.

The starting product is oleic sunflower oil (OSO) of formula:

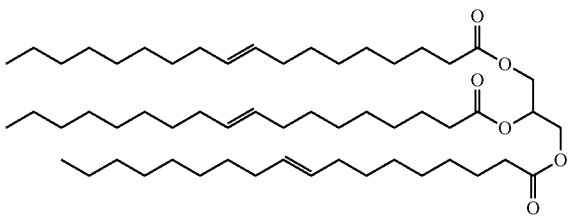 [SMILES: CCCCCCCC/C=C/CCCCCCCC(=O)OCC(COC(=O)CCCCCCC/C=C/CCCCCCCC)OC(=O)CCCCCCC/C=C/CCCCCCCC]

In a jacketed reactor are introduced 604.8 g of oleic sunflower oil (OSO) (ITERG, M=884.82 g·mol$^{-1}$–water content=0.35% by weight) with 188.2 g of absolute ethanol (JT Baker–M=46.07 g·mol$^{-1}$). The whole is mixed with stirring at 650 rpm$^{-1}$ and heated to 65° C. 6.7211 g of MeONa (Aldrich–M=54.02 g·mol$^{-1}$) are then added into the reactor and a change in color of the product and the appearance of instantaneous turbidity are then noticed. The whole was then left to react for 1 h at 70° C.

The resulting reaction mixture was then transferred into a separating funnel in order to remove the glycerol and evaporate the ethanol. Neutralization was then carried out with a few drops of HCl and then washing with water until neutrality. Finally, the residual water was distilled in the Rotavapor.

532.1 g of sunflower oil ethyl ester of the aforementioned formula (1) were obtained with a water content of 0.35% by weight.

According to the characterization by gas phase chromatography which was carried out, a composition was obtained comprising 98.2% by weight of ethyl ester.

Example 1bis

Preparation of Oleic Sunflower Oil Ethyl Esters

This example relates to the preparation of compound (1) of the aforementioned Example 1 from oleic sunflower oil (OSO).

In a jacketed reactor are introduced 502.8 g of oleic sunflower oil (OSO) (ITERG) with 161.5 g of absolute ethanol (JT Baker–M=46.07 g·mol$^{-1}$). The whole is mixed with stirring at 650 rpm$^{-1}$ and heated to 65° C. 5.5880 g of MeONa (Aldrich–M=54.02 g·mol$^{-1}$) are then added into the reactor and a change in color of the product and the appearance of instantaneous turbidity are then noticed. The whole is then left to react for 5 h at 70° C.

The resulting reaction mixture was then transferred into a separating funnel in order to remove the glycerol and evaporate the ethanol. Neutralization was then carried out with a few drops of HCl and then washing with water until neutrality. Finally, the residual water was distilled in the Rotavapor.

455.2 g of sunflower oil ethyl ester of the aforementioned formula (1) was thereby obtained with a water content of 0.29% by weight.

According to characterization by gas phase chromatography which was carried out, a composition was obtained comprising 97.4% by weight of ethyl ester.

Example 2

Preparation of Oleic Sunflower Oil Butanediol Esters

This example relates to the preparation of the compound (2) of the following formula:

This is a compound of formula (IV) in which $R_1$ represents an alkyl group comprising 8 carbon atoms, $A_1$ represents an alkylene radical comprising 7 carbon atoms, $A_2$ represents a butylene radical and $Y_1$ represents H or a group of formula ($A_1$) as defined above.

The starting product is the compound (1) as obtained in Example 1.

In a reactor (500 mL) are introduced 301.5 g of compound (1) (OSOEE) with 43.1 g (0.5 mol) of 1,4-butanediol (Aldrich) (compound of formula (III) with $A_2$=butylenes). The whole is heated to 65° C. 3.3602 g of MeONa (Aldrich) are then added into the reactor and a change in color of the product (opaque yellow) is then noticed. The whole is then left to react for 6 hours at 70-75° C. with stirring (650 rpm$^{-1}$) at a pressure from 800 to 300 mbars.

Neutralization was then carried out with few drops of HCl and then with washing with water in order to remove the traces of butanediol until neutrality. Finally the residual water was distilled in the Rotavapor.

279 g of sunflower oil butanediol ester of the aforementioned formula (2) were thereby obtained with a water content of 0.22% by weight. The product of formula (2) is in the form of a limpid yellow liquid and has an acid index of 3.58%.

According to characterization by gas phase chromatography which was carried out, a composition was obtained comprising:

after 1 hour: 70% by weight of diesters (compound (2) with $Y_1$=($A_1$)), 11.1% by weight of monoesters (compound (2) with $Y_1$=H) and 18.9% of compound (1).

after 7 hours: 74.5% by weight of diesters (compound (2) with $Y_1$=($A_1$)), 12.5% by weight of monoesters (compound (2) with $Y_1$=H) and 16% of compound (1).

Moreover, with additional purifications it was possible to increase the yield and notably obtain up to 85% by weight of diesters, and this by carrying out distillation of the residual monoesters.

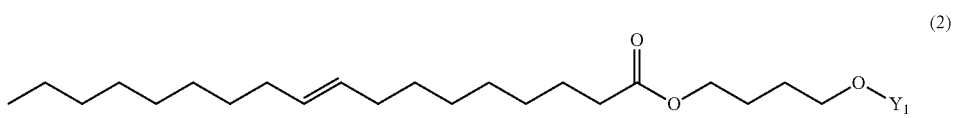

(2)

Example 3

Preparation of Oleic Sunflower Oil Epoxidized Butanediol Esters

This example relates to the preparation of the compound (3) of the following formula:

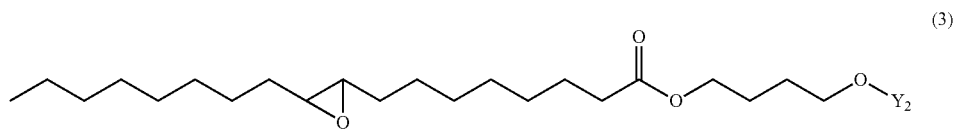

(3)

This is a compound of formula (V) in which $R_1$ represents an alkyl group comprising 8 carbon atoms, $A_1$ represents an alkylene radical comprising 7 carbon atoms, $A_2$ represents a butylenes radical and $Y_2$ represents H or a group of formula $(A_2)$ as defined above.

The starting product is the compound (2) as obtained in Example 2 having the following composition: 83.7% by weight of diesters, 8.80% by weight of monoesters and 7.50% by weight of ethyl ester (compound (1)).

In a reactor (250 mL) are introduced 79.7 g of compound (2) butanediol esters) with 7 g (0.3 mol) of formic acid HCOOH (BAKER) at 45° C. for 1 hour at 500 rpm$^{-1}$. Hydrogen peroxide was then added with a dropping funnel dropwise for 10 minutes (36.7 g (2 moles) of 50% $H_2O_2$ (BAKER)). The whole was then left to react for 2 hours at 75° C. with stirring at 650 rpm$^{-1}$. As the reaction is exothermic, the medium was cooled with a bath of cold water.

Washing with water was then carried out until neutrality of the washing waters. Finally, the residual water was distilled in the Rotavapor.

79.3 g of sunflower oil epoxidized butanediol esters of the aforementioned formula (3) were thereby obtained. The product of formula (3) is in the form of a white solid at room temperature and has an acid index of 1.95%.

According to the characterization by gas phase chromatography which was carried out, a composition was obtained comprising 86.8% by weight of diesters (compound (3) with $Y_2=(A_2)$)) 7.3% by weight of monoesters (compound (3) with $Y_2=H$) and 5.9% by weight of compound (1).

Example 4

Preparation of the Diol (4)

This example relates to the preparation of the compound (4) of the following formula:

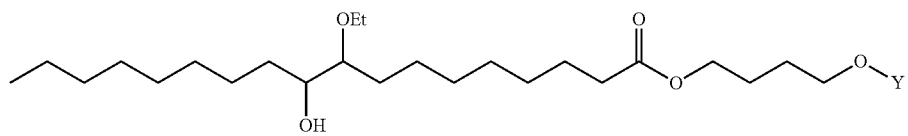

This is a compound of formula (I) in which $R_1$ represents an alkyl group comprising 8 carbon atoms, $A_1$ represents an alkylene radical comprising 7 carbon atoms, $A_2$ represents a butylene radical, R' represents an ethyl group and Y represents H or a group of formula (A) as defined above.

The starting product is the compound (3) as obtained in Example 3 having the following composition: 86.8% by weight of diesters, 7.3% by weight of monoesters and 5.9% by weight of ethyl ester (compound (1)).

In a reactor (250 mL) are introduced 60.2 g of compound (3) (butanediol epoxidized esters) with 2.4 g (4% by weight) of Amberlyst (Aldrich) resin and 112.6 g (15 moles) of absolute ethanol (BAKER). The whole was left to react at 70° C. for 4 hours at 500 rpm. The resin was then filtered on a Büchner and finally the residual ethanol was distilled in the Rotavapor.

53.6 g of the polyol of the aforementioned formula (4) were thereby obtained. The product of formula (3) is in the form of a pale yellow liquid and has an acid index of 1.37%.

According to the characterization by gas phase chromatography which was carried out, a composition was obtained comprising less than 0.5% by weight of butanediol, 82.0% by weight of diesters (compound (1) with Y=(A)), 7.6% by weight of monoesters (compound (1) with Y=H) and 10.4% by weight of compound (1).

The compound (4) was analyzed by IR spectroscopy and an OH band was observed at 3 461.76 cm$^{-1}$ and a secondary alcohol band at 1 087.24 cm$^{-1}$.

Example 5

Preparation of Castor Oil Ethyl Esters

This example relates to the preparation of the compound (5) of the following formula:

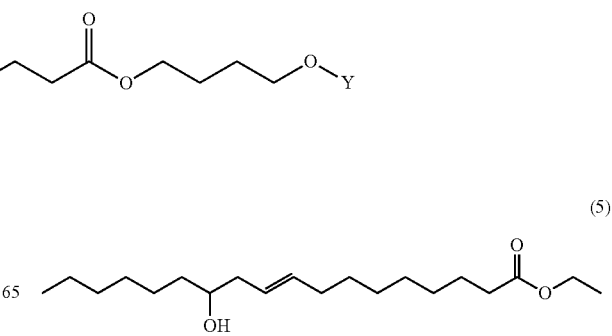

(5)

This is a compound of formula (II') in which R"₁ represents an alkyl group comprising 8 carbon atoms and substituted with an OH group (on the carbon 7), A₁ represents an alkylene radical comprising 7 carbon atoms and R₂ represents an ethyl group.

The starting product is castor oil with the formula:

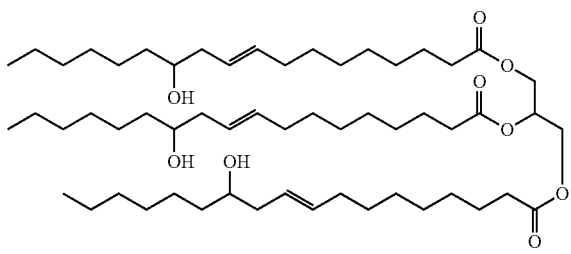 [SMILES: CCCCCCC(O)C/C=C/CCCCCCCC(=O)OCC(COC(=O)CCCCCCC/C=C/CC(O)CCCCCC)OC(=O)CCCCCCC/C=C/CC(O)CCCCCC]

In a jacketed reactor (1 liter) were introduced 402.4 g of castor oil (ITERG, M=928 g·mol⁻¹–water content=0.35% by weight) with 405.4 g of absolute ethanol (JT Baker–M=46.07 g·mol⁻¹). The whole is mixed with stirring at 650 rpm⁻¹ and heated to 65° C. 4.5214 g of MeONa (Aldrich–M=54.02 g·mol⁻¹) are then added into the reactor and a change in color of the product and the appearance of instantaneous turbidity are then noticed. The whole is left to react for 30 minutes at 50° C.

The resulting reaction mixture was then transferred into a separating funnel in order to remove the glycerol and evaporate the ethanol. Neutralization was then carried out with a few drops of HCl and then washing with water until neutrality. Finally, the residual water was distilled in the Rotavapor.

360.2 g of castor oil ethyl ester of the aforementioned formula (5) were thereby obtained with a water content of 0.23% by weight.

According to the characterization by gas phase chromatography which was carried out, a composition was obtained comprising 93.8% by weight of ethyl ester.

Example 6

Preparation of Castor Oil Butanediol Esters

This example relates to the preparation of the compound (6) of the following

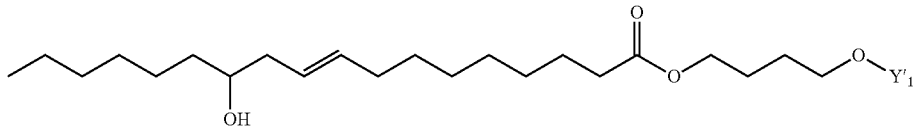

This is a compound of formula (IV') in which R"₁ represents an alkyl group comprising 8 carbon atoms and substituted with an OH group (on the carbon 7), A₁ represents an alkylene radical comprising 7 carbon atoms, A₂ represents a butylenes radical and Y'₁ represents H or a group of formula (A'₁) as defined above.

The starting product is the compound (5) as obtained in Example 5.

In a reactor (500 mL) are introduced 300.5 g of compound (5) with 43.5 g (0.5 mol) of 1,4-butanediol (Aldrich) (compound of formula (III) with A₂=butylene). The whole is heated to 65° C. 3.6005 g of MeONa (Aldrich) are then added into the reactor and a change in color of the product (opaque yellow) was then noticed. The whole is then left to react for 6 hours at 70-75° C. with stirring (650 rpm⁻¹) at a pressure from 800 to 2 mbars.

Neutralization was then carried out with a few drops of HCl and then washing with water in order to remove the butanediol traces until neutrality. Finally, the residual water was distilled in the Rotavapor.

260 g of castor oil butanediol ester of the aforementioned formula (6) were thereby obtained with a water content of 0.30% by weight. The product of formula (6) is in the form of a yellow liquid and has an acid index of 5.05%.

According to the characterization by gas phase chromatography which was carried out, a composition was obtained comprising 43.9% by weight of diesters (compound (6) with Y'₁=(A'₁)), 30.4% by weight of monoesters (compound (6) with Y'₁=H) and 25.7% by weight of compound (5).

Example 7

Preparation of Epoxidized Sunflower Oil Ethyl Esters

This example relates to the preparation of the compound (7) of the following

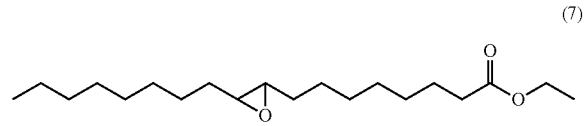 [SMILES: CCCCCCCCC1OC1CCCCCCCC(=O)OCC]

This is a compound of formula (IV"-2) in which R₁ represents an alkyl group comprising 8 carbon atoms, A₁ represents an alkylene radical comprising 7 carbon atoms and R₂ represents an ethyl group.

The starting product is the oleic sunflower oil ethyl ester compound of Example 1bis.

In a reactor (1 L) are introduced 399.6 g of the compound (1) of Example 1 bis (oleic sunflower oil ethyl ester—OSOEE) and 20.1 g of formic acid and the whole was left to react at 45° C. for 1 hour at 500 rpm⁻¹. Next hydrogen peroxide was added dropwise with a dropping funnel for 40 minutes (199.2 of H₂O₂ (BAKER)). The whole was then left to react for 2 hours at 75° C. with stirring at 650 rpm⁻¹. As the reaction is exothermic, the medium was cooled with a cold water bath.

Washing with water was then carried out until neutrality of the washing waters. Finally, the residual water was distilled in the Rotavapor.

410.3 g of oleic sunflower oil epoxidized ethyl esters of the aforementioned formula (7) were thereby obtained. The product of formula (7) is in the form of an orangey liquid and has an acid index of 0.79%, as well as a water content of 0.41%.

Example 8

Preparation of the Diol (8)

This example relates to the preparation of the compound (8) of the following

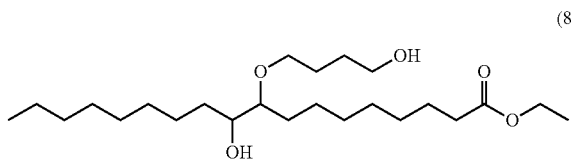
(8)

This is a compound of formula (I"-1) in which $R'_1$ represents an alkyl group comprising 8 carbon atoms, $A_2$ represents a butylene radical, $A_1$ represents an alkylene radical comprising 7 carbon atoms and $R_2$ represents an ethyl group.

The starting product is the epoxidized oleic sunflower oil ethyl ester compound of Example 7.

In a reactor (2 L) 301.2 g of compound (7) are introduced with 12 g (4% by weight) of Amberlyst resin (Aldrich) and 1 201.1 g of distilled 1,4-butanediol (Aldrich). The whole as left to react at 70° C. for 4 hours at 500 rpm$^{-1}$.

The butanediol was distilled at 120-150° C. under 30 mbars and the whole was washed with water for removing the traces of butanediol. The resin was then filtered on a Büchner and, finally the residual ethanol was distilled in the Rotavapor.

270.3 g of the polyol of the aforementioned formula (8) were thereby obtained. The product of formula (8) has an acid index of 0.27% and a hydroxyl index of 255.8 mg KOH/g.

According to the characterization by gas phase chromatography which was carried out, a composition was obtained, comprising less than 0.1% by weight of butanediol, 22% by weight of diesters, 71.7% by weight of monoesters (compound 8) and 6.1% by weight of compound (1).

Example 9

Preparation of Erucic Rape Seed Oil Ethyl Esters

This example relates to the preparation of the compound (9) of the following

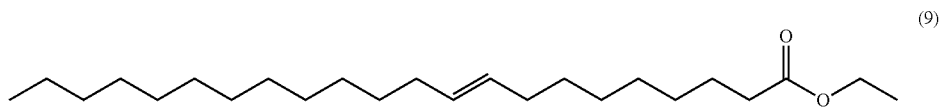 [SMILES: CCCCCCCCCCCC/C=C/CCCCCCCC(=O)OCC]
(9)

This is a compound of formula (II) in which $R_1$ represents an alkyl group comprising 12 carbon atoms, $A_1$ represents an alkylene radical comprising 7 carbon atoms and $R_2$ represents an ethyl group.

The starting product is erucic rape seed oil of formula:

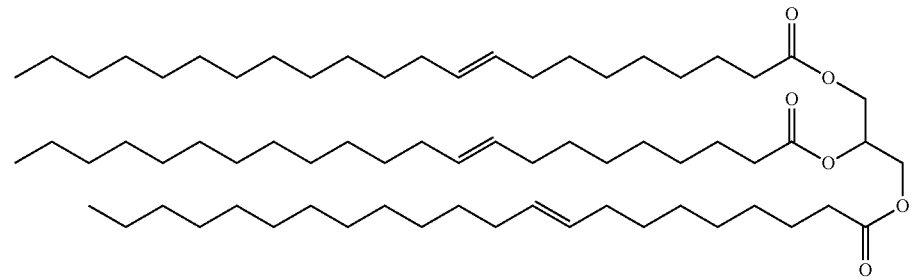 [SMILES: CCCCCCCCCCCC/C=C/CCCCCCCC(=O)OCC(COC(=O)CCCCCCC/C=C/CCCCCCCCCCCC)OC(=O)CCCCCCC/C=C/CCCCCCCCCCCC]

In a jacketed reactor (1.5 liter) are introduced 1 004.7 g of erucic rape seed oil (ERO) (ITERG, M=951.8 g·mol$^{-1}$-water content=0.35% by weight) with 290.7 of absolute ethanol (JT Baker–M=46.07 g·mol$^{-1}$). The whole is mixed with stirring at 650 rpm$^{-1}$ and heated to 65° C. 11.1 g of MeONa (Aldrich–M=54.02 g·mol$^{-1}$) were then added into the reactor and a change in the color of the product and the appearance of instantaneous turbidity was then noticed. The whole is then left to react for 1 hour at 70° C.

The resulting reaction mixture was then transferred into a separating funnel in order to remove the glycerol and evaporate the ethanol. Neutralization was then carried out with a few drops of HCl and then washing with water until neutrality. Finally the residual water was distilled in the Rotavapor.

1 026.8 g of rape seed oil ethyl ester of the aforementioned formula (9) of the were thereby obtained with a water content of 0.27% by weight and an acid index of 1.04%.

According to the characterization by gas phase chromatography which was carried out, a composition was obtained comprising 98.48% by weight of ethyl ester.

Example 10

Preparation of Epoxidized Rape Seed Oil Ethyl Esters

This example relates to the preparation of the compound (10) of the following formula:

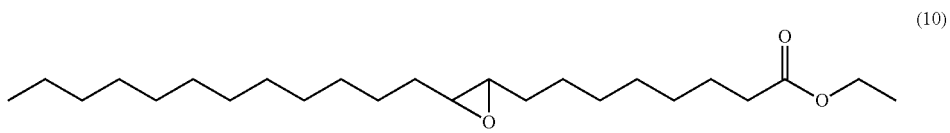 [SMILES: CCCCCCCCCCCCC1OC1CCCCCCCC(=O)OCC]

This is a compound of formula (IV"-2) in which $R_1$ represents an alkyl group comprising 12 carbon atoms, $A_1$ represents an alkylene radical comprising 7 carbon atoms and $R_2$ represents an ethyl group.

The starting product is the rape seed oil ethyl ester compound of Example 9.

In a reactor (1 L) are introduced 400.5 g of compound (9) (rape seed oil ethyl ester—ROEE) and 23.12 g of formic acid and the whole is left to react at 45° C. for 1 hour at 500 rpm. Hydrogen peroxide was then added dropwise with a dropping funnel for 40 minutes (211.1 g of $H_2O_2$ (BAKER)). The whole was then left to react for 3 hours at 75° C. with stirring at 650 rpm$^{-1}$. As the reaction is exothermic, the medium was cooled with a cold water bath.

Washing with water was then carried out until neutrality of the washing waters. Finally, the residual water was distilled in the Rotavapor.

410.2 g of erucic castor oil epoxidized ethyl esters of the aforementioned formula (10) were thereby obtained. The product of formula (10) is in the form of a white solid at room temperature and has an acid index of 1.08%, as well as a water content of 0.22%.

Example 11

Preparation of the Diol (11)

This example relates to the preparation of the compound (11) of the following formula:

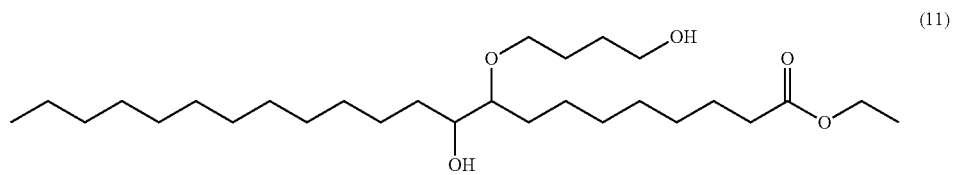 [SMILES: CCCCCCCCCCCCC(O)C(CCCCCCCC(=O)OCC)OCCCCO]

This is a compound of formula (I"-1) in which $R'_1$ represents an alkyl group comprising 12 carbon atoms, $A_2$ represents a butylene radical, $A_1$ represents an alkylene radical comprising 7 carbon atoms and $R_2$ represents an ethyl group.

The starting product is the epoxidized erucic rape seed oil ethyl ester compound of Example 10.

In a reactor (2 L) 350.2 g of compound (10) are introduced with 14.2 g (4% by weight) of Amberlyst resin (Aldrich) and 1 484.6 g of distilled 1,4-butanediol (Aldrich). The whole was left to react at 70° C. for 4 hours at 500 rpm$^{-1}$.

Two phases were then obtained: the upper phase containing the compound 11 and traces of butanediol and the lower phase containing butanediol and traces of compound (11).

The upper phase was therefore distilled with magnetic stirring in vacuo at 120-140° C. under 30 mbars. The lower phase was also distilled in vacuo and with a flow of dinitrogen without stirring for two days in order to obtain a dark brown product.

The whole was washed with water for removing the traces of butanediol. The resin was then filtered on a Büchner and finally the residual ethanol was distilled in the Rotavapor.

Via the upper phase, 126 g of a pale yellow liquid were obtained with an acid index of 0.69% and a hydroxyl index of 190.4 mg of KOH/g, as well as a water content of 0.64%.

According to the characterization by gas phase chromatography which was carried out, a composition was obtained comprising less than 0.1% by weight of butanediol, 6.9% by weight of diesters, 89.1% by weight of monoesters (compound 11), 0.7% by weight of triglycerides and 3.3% by weight of compound (9).

Via the lower phase, 135 g of a dark brown liquid were obtained with a water content of 0.35%.

According to the characterization by gas phase chromatography which was carried out, a composition was obtained comprising less than 0.3% by weight of butanediol, 11.4% by weight of diesters, 87.7% by weight of monoesters (compound 11), 0.4% by weight of triglycerides and 0.3% by weight of compound (9).

Example 12

Preparation of Polymers from Polyols of Formula (I')

By applying the same procedures as in the aforementioned examples 1 to 6, the following compounds were also synthesized:

Synthesis of Polymers from the Polyol

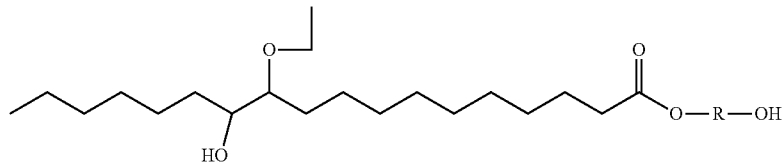

| Group R | $C_3H_6$ | $C_4H_8$ | $C_6H_{12}$ |
|---|---|---|---|
| Reaction time | 5 h | 5 h | 5 h |
| $M_w$ | 20,000 g/mol | 20,000 g/mol | 18,000 g/mol |
| IP | 1.4 | 1.5 | 1.3 |

Synthesis of Polymers from the Polyol

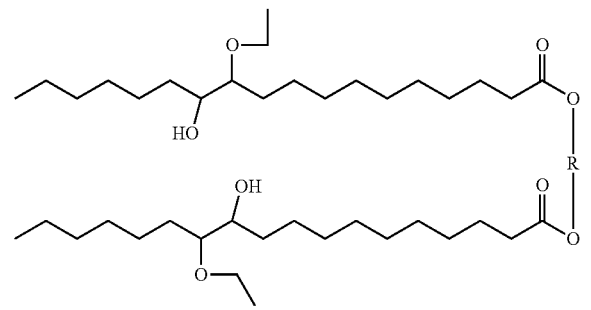

| Group R | $C_3H_6$ | $PEG_{300}$ | $PEG_{600}$ |
|---|---|---|---|
| Reaction time | 7 h | 8 h | 10 h |
| $M_w$ | 15,000 g/mol | 14,000 g/mol | 14,000 g/mol |
| IP | 1.4 | 1.5 | 1.3 |

The polyols of the invention are used for preparing polymers for example by reaction with isocyanates. The applied procedure is described hereafter and may be applied to any polyol and any isocyanate.

In a reactor of 100 mL were added the polyol of the invention and the catalyst and then the isocyanate (in particular IPDI was added into the reactor via a funnel. The temperature of the mixture was maintained at 60° C. by heating.

From the Polyol Monoester with $R=O_3H_6$ 2 g of monoester were introduced into a 100 mL reactor in the presence of 2 mg of DBTDL (LCPO) (dibutyltin dilaurate) (0.1% by weight). And then 1.1 g of IPDI (Aldrich-M=222.29 g·mol$^{-1}$) (isophorone diisocyanate) (1 equivalent) were introduced. The mixture was placed with magnetic stirring for 5 hours.

The kinetics of the reaction were tracked by IR analysis which allowed observation of the disappearance of the band N=C at 2 269.94 cm$^{-1}$ and the appearance of the band N—H at 3 350 cm$^{-1}$. The obtained polymer was analyzed by steric exclusion chromatography (the obtained molar masses are listed in the tables above).

The procedure is unchanged for the cases when $R=C_4H_{10}$ and $R=O_6H_{12}$.

From the Polyol Diester with $R=C_3H_6$ 2 g of diester were introduced into a 100 mL reactor in the presence of 2 mg of DBTDL (LCPO) (dibutyltin dilaurate) and then 586 mg of IPDI (Aldrich-M=222.29 g·mol$^{-1}$) (isophorone diisocyanate) (0.5 equivalent) were introduced. The mixture was placed with magnetic stirring for 7 hours.

The kinetics of the reaction were tracked by IR analysis which allowed observation of the disappearance of the band N=C at 2 269.94 cm$^{-1}$ and the appearance of the band N—H at 3 350 cm$^{-1}$. The obtained polymer was obtained by steric exclusion chromatography (the obtained molar masses are listed in the tables above).

The procedure is unchanged for the cases when $R=PEG_{300}$ and $R=PEG_{500}$.

Example 13

Preparation of Polyurethanes from the Diol 8

The polyols of the invention are used for preparing polymers for example by reaction with isocyanates. The applied procedure is described hereafter and may be applied to any polyol and any isocyanate.

In a reactor of one liter, the polyol of the invention and the catalyst were added and then the isocyanate (in particular IPDI or HMDI) was added into the reactor via a funnel. The whole was then stirred at 80 rpm$^{-1}$ under dinitrogen in order to homogenize the mixture. The appearance of bubbles was then observed in the reaction mixture and the temperature of the mixture was maintained at 60° C. by heating.

The kinetics of the reaction were tracked by IR analysis which allowed observation of the disappearance of the band N=C at 2 269.94 cm$^{-1}$ and the appearance of the band N—H at 3 350 cm$^{-1}$.

More particularly, this procedure was applied by using as a polyol, the diol 8 of Example 8 and by varying the nature of the isocyanate (IPDI and HMDI), as well as the reaction time and the OH:NCO ratio.

The catalyst used is DBTDL (LCPO) (dibutyltin dilaurate) at 0.1% by weight.

The obtained results are summarized hereafter in Tables 1 and 2.

TABLE 1 corresponds to the synthesis of polyurethane by reaction with IPDI
(Aldrich – M = 222.29 g·mol$^{-1}$)(isophorone diisocyanate):

| | | | | | Viscosity (cst) | | | |
|---|---|---|---|---|---|---|---|---|
| | | Solubility | | | 80° C. | | 100° C. | |
| | | (DCM, | | GPC | Shearing (s$^{-1}$) | | | |
| | Reaction | THF, | IR | Analysis | | | | |
| No | OH:NCO | time (h) | DMF) | Analysis | (Mw) | 1 | 10 | 1 | 10 |
| 1 | 1:0.2 | 7 | soluble | No isocyanate band | 1 830 | — | 9.5 | — | 4.5 |
| 2 | 1:0.3 | 7 | soluble | No isocyanate band | 2 300 | — | 23.5 | — | 11.5 |
| 3 | 1:0.5 | 7 | soluble | No isocyanate band | 5 240 | — | 160 | — | 70 |
| 4 | 1:0.65 | 7 | soluble | No isocyanate band | 10 820 | 1050 | 775 | — | 280 |
| 5 | 1:0.69 | 12 | soluble | No isocyanate band | 12 570 | — | — | — | — |

DCM: dichloromethane
THF: tetrahydrofurane
DMF: dimethylformamide
The suitable viscosities are obtained for an OH:NCO ratio of less than 1:0.70.

TABLE 2 corresponds to the synthesis of polyurethane by reaction with HMDI
(hexamethylene diisocyanate):

| | | | | | Viscosity (cst) | | | |
|---|---|---|---|---|---|---|---|---|
| | | Solubility | | | 80° C. | | 100° C. | |
| | | (DCM, | | GPC | Shearing (s$^{-1}$) | | | |
| | Reaction | THF, | IR | Analysis | | | | |
| No | OH:NCO | time (h) | DMF) | Analysis | (Mw) | 1 | 10 | 1 | 10 |
| 1 | 1:0.3 | 6 | soluble | No isocyanate band | 2 740 | — | 31.7 | — | 14.5 |
| 2 | 1:0.5 | 6 | soluble | No isocyanate band | 7 200 | 287 | 385 | 93 | 188 |
| 3 | 1:0.65 | 9 | soluble | No isocyanate band | 13 550 | 3 474 | 3 055 | 879 | 891 |

Example 14

Preparation of a Diol of Formula (I-2) with Two Secondary Alcohol Functions

The procedure described hereafter was used for synthesizing compounds of formula (I-2), $A_1$ representing a $C_7H_{14}$ radical and $R_1$ representing an alkyl group comprising 9 carbon atoms.

In formula (I-2), $A_2$ may represent a radical selected from the following radicals: $C_3H_6$, $C_4H_8$, $C_5H_{10}$, $C_6H_{12}$, $H_2C$—$(CH_2OCH_2)_6$—$CH_2$, $H_2C$—$(CH_2OCH_2)_{13}$—$CH_2$, $H_2C$—$(CH_2OCH_2)_{45}$—$CH_2$ or $H_2C$—$C_6H_4$—$CH_2$.

Transesterification Step:

The diesters stem from transesterification of an oleic methyl ester and of a diol (propanediol, butanediol, pentanediol, hexanediol, polyoxyethylene (300 g/mol, 600 g/mol and 2000 g/mol)). The synthesis involves 0.1 mol of oleic methyl ester and 0.05 mol of diol, in the presence of magnesium oxide MgO (catalyst, 1% by mass based on the methyl ester mass). The medium was kept with stirring at 160° C., under nitrogen flow, for 7 hours. The methanol formed by the reaction was removed from the reaction medium by means of a Dean Stark trap. The formation of the diester was followed via $^1$H MNR. After 7 hours, the medium was placed at 200° C. in a dynamic vacuum for 1 hour in order to remove the oleic methyl ester and the residual diols. The catalyst was removed by filtration.

For the synthesis of the diester from methyl ester and 1,4-benzenedimethanol ($A_2$=$H_2C$—$C_6H_4$—$CH_2$), the temperature of the medium during the reaction was 140° C. in order not to sublimate the 1,4-benzenedimethanol.

Epoxidation Step:

10 mmol of diester synthesized previously were mixed with 3 mmol of formic acid (HCOOH). The mixture was heated to 40° C. for 1 hour. And then 10 mmol of hydrogen peroxide ($H_2O_2$) were added dropwise. The temperature was raised to 70° C. for 2 hours. The formation of the epoxide was followed by $^1$H MNR. When the reaction is completed, it is proceeded with water-dichloromethane washing in order to remove the peracid.

Hydroxylation Step:

For the step for opening the epoxide, 10 mmol of epoxidized diesters were dissolved in 100 mmol of ethanol, in the presence of an ion exchange resin (Amberlyst 15 Dry, 4% by mass based on the mass of the diesters). The reaction medium was placed with stirring, at 75° C. for 20 hours. The opening of the epoxide was followed by $^1$H MNR. When the reaction was complete, the catalyst was removed by filtration. The excess ethanol was then evaporated under low pressure. The hydroxylated diesters were then analyzed with $^1$H MNR and with steric exclusion chromatography. Their hydroxyl index was determined.

Example 15

Preparation of a Diol of Formula (I-1) with Two Secondary Alcohol Functions

The procedure described hereafter was used for synthesizing compounds of formula (I-1), $A_1$ representing a $C_7H_{14}$ radical and $R_1$ representing an alkyl group comprising 9 carbon atoms.

In the formula (I-1), $A_2$ may represent a radical selected from the following radicals: $C_3H_6$, $C_4H_8$, $C_5H_{10}$, $C_6H_{12}$, $H_2C$—$(CH_2OCH_2)_6$—$CH_2$, $H_2C$—$(CH_2OCH_2)_{13}$—$CH_2$, $H_2C$—$(CH_2OCH_2)_{45}$—$CH_2$ or $H_2C$—$C_6H_4$—$CH_2$.

The synthesis procedures are the same as those indicated for example 14, except for the transesterification step. The synthesis involves 0.1 mol of oleic methyl ester and 1.5 mol of diol, in order to promote formation of monoesters relatively to diesters.

Example 16

Preparation of Bisepoxide Compounds of Formula (V-3)

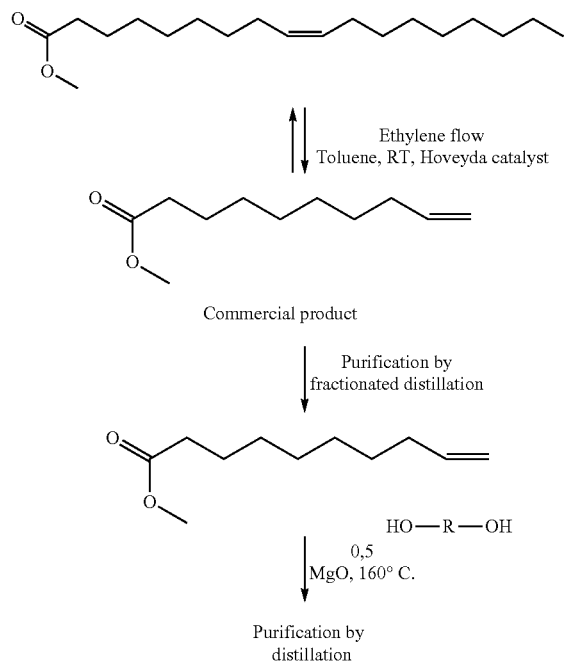

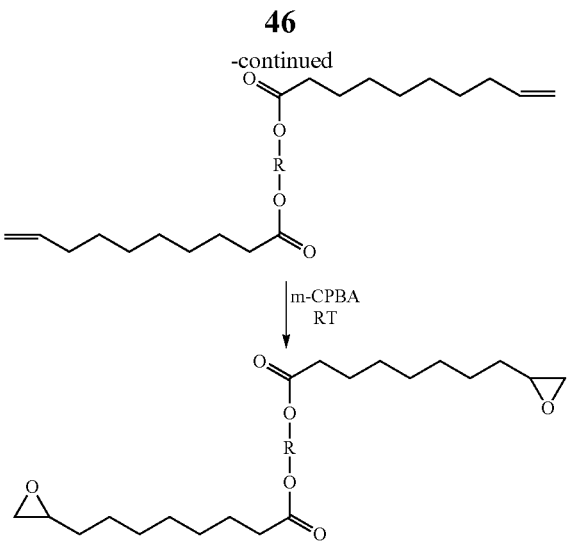

The first step consisted of cutting the carbonaceous chain of the oleic methyl ester at the internal double bond in order to obtain an internal double bond. A metathesis reaction between ethylene and the internal double bond of the oleic methyl ester in the presence of Hoveyda catalyst lead to the formation of decene and of methyl 10-undecenoate. This reaction took place with stirring at room temperature. In the equilibrium state, the medium consists of 48% of initial oleic methyl ester, 26% of decene and 26% of methyl 10-undecenoate. The latter was extracted by distillation in vacuo: the first fraction at 100° C. contained decene; methyl 10-undecenoate was recovered when the temperature reached 180° C. The residue consisted of oleic methyl ester.

It was then proceeded with a reaction for transesterification of methyl 10-undecenoate with a diol (aliphatic, aromatic diol, phenol of natural origin, etc.). The reaction took place in vacuo in the presence of 0.5 equivalent of diol in order to promote formation of diesters; it was catalyzed with 1 wt % of magnesium oxide. The temperature of the medium was raised to 160° C., the produced methanol was removed continuously by means of a Dean Stark trap. After 7 hours, the temperature was raised to 180° C. in order to remove the residual methyl 10-undecenoate.

The last step consisted in the epoxidation of the double bonds of the product obtained by transesterification. It was carried out in the presence of metachloroperbenzoïc acid (m-CPBA) (1.2 equiv. per double bond), in dichloromethane at room temperature. The conversion of the double bonds was total after 3 hours. The excess m-CPBA was reduced into the corresponding carboxylic acid with a saturated solution of sodium sulfate. The organic phase was extracted with dichloromethane and then the residual carboxylic acid was transformed into sodium chlorobenzoate (soluble in water) by two washings with a saturated solution of sodium bicarbonate.

Example 17

Preparation of Oleic Sunflower Oil Ethyl Esters

This example relates to the preparation of the compound (1) of the aforementioned Example 1 from oleic sunflower oil (OSO).

In a jacketed reactor are introduced 1 001.2 g of oleic sunflower oil (OSO) (ITERG, M=884.82 g·mol$^{-1}$–water content=0.35% by weight) with 314.0 g of absolute ethanol (JT Baker–M=46.07 g·mol$^{-1}$). The whole is mixed with stirring at 650 rpm$^{-1}$ and heated to 65° C. 11.5 g of MeONa (Aldrich–M=54.02 g·mol$^{-1}$) were then added into the reactor and a change in color of the product and the appearance of instantaneous turbidity were then noticed. The whole was then left to react for 1 hour at 70° C.

The resulting reaction mixture was then transferred into a separating funnel in order to remove the glycerol and evaporate the ethanol. Neutralization was then carried out with a few drops of HCl and then washing with water until neutrality. Finally, the residual water was distilled in the Rotavapor.

1 056.5 g of sunflower oil ethyl ester of the aforementioned formula (1) with a water content of 0.15% by weight were thereby obtained.

According to the characterization by gas phase chromatography which was carried out, a composition was obtained comprising 97.8% by weight of ethyl ester.

Example 18

Preparation of Epoxidized Sunflower Oil Ethyl Esters

This example relates to the preparation of the compound (7) of Example 7 from the compound (1) of Example 18.

In a reactor (2 L) 800.5 g of the compound (7) of Example 7 (oleic sunflower oil ethyl ester—OSOEE) were introduced and 39.4 gl of formic acid and the whole was left to react at 45° C. for 1 hour at 500 rpm$^{-1}$. Hydrogen peroxide was then added dropwise with a dropping funnel for 36 minutes (355.5 g of H$_2$O$_2$ (BAKER)). The whole was then left to react for 2 hours at 75° C. with stirring at 650 rpm$^{-1}$. As the reaction is exothermic, the medium was cooled with a cold water bath.

Washing with water was then carried out until neutrality of the washing waters. Finally, the residual water was distilled in the Rotavapor.

1 056.5 g of oleic sunflower epoxidized ethyl esters of the aforementioned formula (7) were thereby obtained. The product of formula (7) is in the form of a pale yellow liquid and has a water content of 0.11%.

Example 19

Preparation of the Diol (8)

This example relates to the preparation of the diol (8) of Example 8 from the compound (7) of Example 1.

In a reactor (2 L) were introduced 100.4 g of compound (7) with 4.1 g (4% by weight) of Amberlyst resin (Aldrich) and 416.1 g of distilled 1,4-butanediol (Aldrich). The whole was left to react at 70° C. for 4 hours at 650 rpm$^{-1}$.

The whole was washed with water for removing the traces of butanediol, and finally the residual ethanol was distilled in the Rotavapor.

93.0 g of the polyol of the aforementioned formula (8) were thereby obtained.

According to the characterization by HPLC chromatography which was carried out, a composition was obtained, comprising 1.1% by weight of butanediol, 6.8% by weight of diesters, 70.5% by weight of monoesters (compound 8) and 2.0% by weight of compound (1).

Example 20

Preparation of Epoxidized Rape Seed Oil Ethyl Esters

This example relates to the preparation of the compound (10) of Example 10 from erucic rape seed oil ethyl esters.

In a reactor (1 L) are introduced 400.6 g of compound (9) (rape seed oil ethyl ester—ROEE) and 27.0 g of formic acid and the whole was left to react at 45° C. for 1 hour at 500 rpm$^{-1}$. Hydrogen peroxide was then added dropwise with a dropping funnel for 45 minutes (211.1 of H$_2$O$_2$ (BAKER)). The whole was then left to react for 3 hours at 75° C. with stirring at 650 rpm$^{-1}$. As the reaction is exothermic, the medium is cooled with a cold water bath.

Washing with water was then carried out until neutrality of the washing waters. Finally, the residual water was distilled in the Rotavapor.

391.1 g of erucic castor oil epoxidized ethyl esters of formula (10) (cf. Example 10) were thereby obtained.

Example 21

Preparation of the Diol (11)

This example relates to the preparation of the compound (11) of Example 11 from the ethyl ester of Example 10 of epoxidized erucic rape seed oil.

In a reactor (2 L) were introduced 350.2 g of compound (10) with 14.3 g (4% by weight) of Amerlyst resin (Aldrich) and 514.5 g of distilled 1,4-butanediol (Aldrich). The whole was left to react at 70° C. for 4 hours at 650 rpm$^{-1}$.

The whole was poured into a separating funnel, in which 200 mL of warm water were added followed by 100 mL of butanol. After stirring and phase separation at rest, two phases were observed. The upper phase was put aside and the lower phase was washed with 2×50 mL of butanol. The upper phases were then grouped, washed with warm water in order to remove the traces of butanediol, and then dried in the Rotavapor.

272.1 g of a pale yellow liquid with a hydroxyl index of 187.9 mg KOH/g, as well as a water content of 0.66% were thereby obtained.

According to the characterization by gas phase chromatography which was carried out, a composition was obtained comprising less than 0.1% by weight of butanediol, 9.2% by weight of diesters and 66.1% by weight of monoesters (compound 11).

Example 22

Synthesis of Polyurethanes from the Diols of Examples 19 and 21

Synthesis Procedure

A three-neck flask (250 mL) with a mechanical stirrer and a nitrogen inlet was loaded with dibutyltin dilaurate (0.003 g, 0.1% by mass based on the monomers), the polyol (from Example 19 or 21) (18.0 g, hydroxyl index=215.9) and with isophorone diisocyanate (IPDI) (6.54 g, OH/NCO=1:0.85). The OH./NCO ratio was calculated on the basis of the hydroxyl index of the polyol. The reaction medium was stirred at room temperature under nitrogen flow and heated to 60° C. for 9 hours. Polymerization was controlled by IR spectroscopy on the basis of the isocyanate band. After completion of the reaction, 0.7 g of octyl dodecanol were added in order to stop the reaction with additional heating for a further 12 hours. The obtained polymer was characterized by IR, MNR and GPC.

The same procedure was applied by using HDMI as a diisocyanate instead of IPDI.

TABLE 3 hereafter illustrates the results obtained for the synthesis of polyurethane by reaction with IPDI or HDMI as an isocyanate and the polyols of Examples 19 and 21:

| Polyol | OH/NCO ratio | diisocyanate | GPC Analysis Mw | Mw/Mn | Viscosity (cst) 30° C. Shearing (1/s) 1 | 10 | 80° C. 1 | 10 | 100° C. 1 | 10 |
|---|---|---|---|---|---|---|---|---|---|---|
| Ex. 19 | 1:0.85 | IPDI | 3280 | 1.61 | 5850* | — | 105 | 93 | — | 31.5 |
| Ex. 19 | 1:0.75 | HMDI | 3210 | 1.35 | 6550* | — | 98 | 92 | 38 | 33 |
| Ex. 19 | 1:0.85 | HMDI | 4160 | 1.47 | — | — | 250 | 220 | 95 | 60 |
| Ex. 21 | 1:0.7 | IPDI | 3730 | 1.32 | — | — | — | — | — | — |

What is claimed is:

1. A method for preparing a polyol fitting the general formula (I):

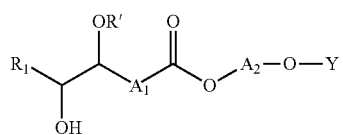

(I)

wherein:
$R_1$ represents H or a linear or branched alkyl group, comprising from 2 to 14 carbon atoms,
R' represents a linear or branched alkyl group, comprising from 1 to 18 carbon atoms,
$A_1$ represents a linear or branched divalent alkylene radical, comprising from 2 to 14 carbon atoms,
$A_2$ represents a linear divalent alkylene radical, comprising from 1 to 10 carbon atoms, if necessary comprising one or more substituents,
Y represents a hydrogen atom or a group of formula (A)

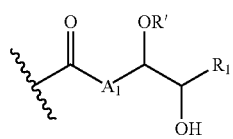

(A)

$A_1$, R' and $R_1$ are as defined above,
said method comprising the following steps:
a) a step for transesterification of a compound of the following formula (II):

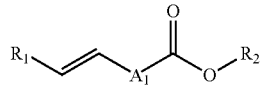

(II)

$R_2$ represents a branched or linear alkyl group comprising from 1 to 10 carbon atoms, and $R_1$ and $A_1$ being as defined above,
with a diol of the following formula (III):

$$HO\text{-}A_2\text{-}OH \quad (III)$$

in order to obtain a compound of the following formula (IV):

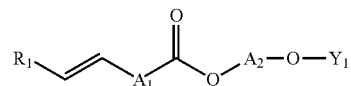

(IV)

$A_1$, $A_2$ and $R_1$ being as defined above in formula (I),
$Y_1$ representing a hydrogen atom or a group of formula ($A_1$)

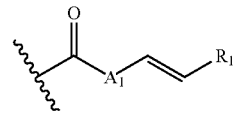

($A_1$)

$A_1$ and $R_1$ being as defined above,
b) a step for epoxidation of the compound of the aforementioned formula (IV) in order to obtain a compound of the following formula (V):

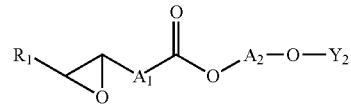

(V)

$A_1$, $A_2$ and $R_1$ being as defined above,
$Y_2$ representing a hydrogen atom or a group of formula ($A_2$)

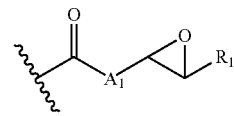

($A_2$)

$A_1$ and $R_1$ being as defined above, c) a step for opening the epoxide ring with an alcohol of formula R'OH, R' being as defined above, in order to obtain a compound of formula (I) as defined above, and d) a step for recovering the compound of formula (I) as defined above.

2. The method for preparing a diol according to claim 1, characterized in that the diol fits the following formula (I-1):

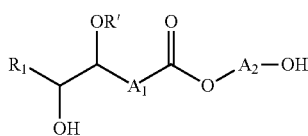

(I-1)

$A_1$, $A_2$, $R_1$ and R' being as defined in claim 1, or the following formula (I-2):

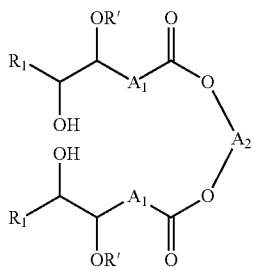

(I-2)

$A_1$, $A_2$, $R_1$ and R' being as defined in claim 1.

3. The method for preparing a polyol according to any of claim 1, wherein step a) is carried out in the presence of a catalyst selected from the group consisting of magnesium oxide, zinc acetate and sodium methanolate.

4. The method for preparing a polyol according to claim 3, wherein step a) is carried out a temperature comprised between from 150 to 200° C. under nitrogen flow.

5. The method according to claim 3, wherein step a) is carried out without solvent.

6. The method for preparing a polyol according to claim 1, wherein step b) is carried out in the presence of a peracid.

7. The method for preparing a polyol according to claim 6, wherein step b) is carried out in the presence of a peracid selected from the group consisting of metachloroperbenzoic acid (m-CPBA) and of magnesium monoperoxyphthalate hexahydrate peracid (MMPP).

8. The method for preparing a polyol according to claim 1, wherein step c) is carried out in the presence of a catalyst selected from the group consisting of an acid catalyst of the proton ion exchange resin, of heterogeneous catalysts, of para-toluenesulfonic acid (PTSA) and of methanesulfonic acid (MSA), at a temperature comprised between from 20° C. to 120° C.

9. The method for preparing a polyol according to claim 8, wherein the temperature is 70° C.

10. A compound fitting the following general formula (I):

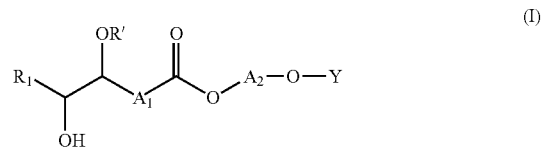

(I)

wherein:

$R_1$ represents a linear or branched alkyl group comprising from 2 to 14 carbon atoms, R' represents a linear or branched alkyl group, comprising from 1 to 18 carbon atoms, $A_1$ represents a linear or branched divalent alkylene radical, comprising from 2 to 14 carbon atoms, $A_2$ represents a linear divalent alkylene radical, comprising from 1 to 10 carbon atoms, if necessary comprising one or more substituents, and Y represents a hydrogen atom or a group of formula (A)

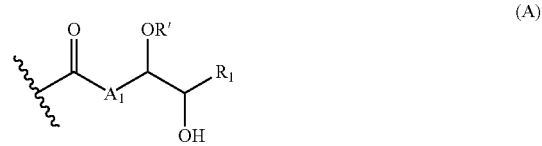

(A)

$A_1$, R' and $R_1$ being as defined above.

11. Intermediate compounds chosen from the group consisting of: —compound (3) having the following formula:

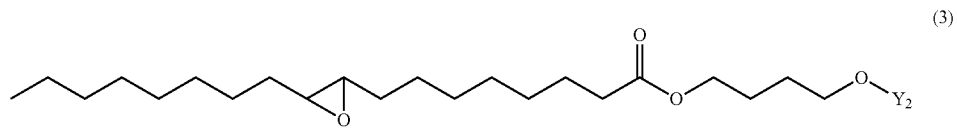

(3)

wherein $Y_2$ represents $A_2$, $A_2$ being as defined in claim 1; and compounds having the following formula:

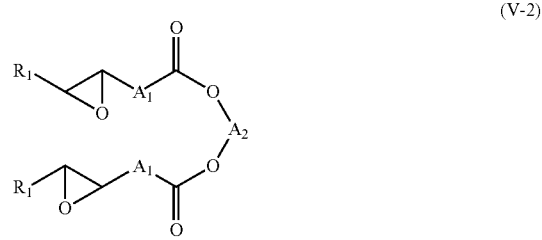

(V-2)

$A_1$ representing a $C_7H_{14}$ radical, $R_1$ representing an alkyl group comprising 9 carbon atoms, and $A_2$ represents a radical selected from the following radicals: $C_3H_6$, $C_4H_8$, $C_5H_{10}$, $C_6H_{12}$, $H_2C$—$(CH_2OCH_2)_6$—$CH_2$, $H_2C$—$(CH_2OCH_2)_{13}$—$CH_2$, $H_2C$—$(CH_2OCH_2)_{45}$—$CH_2$ or $H_2C$—$C_6H_4$—$CH_2$.

12. Polymers as obtained by polymerization of a compound as defined in claim 10 and of a (poly)isocyanate.

* * * * *